(12) United States Patent
Magnasco

(10) Patent No.: US 11,259,747 B2
(45) Date of Patent: Mar. 1, 2022

(54) ADAPTIVE COMPRESSION SLEEVES AND CLOTHING ARTICLES

(71) Applicant: James A. Magnasco, East Boston, MA (US)

(72) Inventor: James A. Magnasco, East Boston, MA (US)

( * ) Notice: Subject to any disclaimer, the term of this patent is extended or adjusted under 35 U.S.C. 154(b) by 320 days.

(21) Appl. No.: 15/640,094

(22) Filed: Jun. 30, 2017

(65) Prior Publication Data
US 2019/0000385 A1    Jan. 3, 2019

(51) Int. Cl.
*A61B 5/00*    (2006.01)
*A61B 5/11*    (2006.01)
(Continued)

(52) U.S. Cl.
CPC .......... *A61B 5/6804* (2013.01); *A61B 5/1107* (2013.01); *A61B 5/4836* (2013.01);
(Continued)

(58) Field of Classification Search
CPC ....... A61B 5/00; A61B 5/0048; A61B 5/0051; A61B 5/0053; A61B 5/04; A61B 5/04001; A61B 5/04002; A61B 5/0059; A61B 5/05; A61B 5/053; A61B 5/0531; A61B 5/103; A61B 5/107; A61B 5/1071; A61B 5/1107; A61B 5/4519; A61B 5/6801; A61B 5/6802; A61B 5/6804; A61B 5/6812; A61B 5/6824; A61B 5/6829; A61B 5/742; A61B 5/7475; A61B 5/4836; A61B 5/0109; A61B 2505/09; A61B 2560/0214; A61B 2560/029; A61B 2560/0462; A61B 2560/0468; A61B 2562/046; A61B 2562/043; A61F 5/0102; A61F 5/0109; A61F 5/0106; A61F 5/0111; A61F 5/0118; A61F 5/0123; A61F 5/013; A61F 2005/0155; A61F 2005/0188; A61F 2007/0029; A61F 2007/0039;
(Continued)

(56) References Cited

U.S. PATENT DOCUMENTS 4,532,013 A * 7/1985 Dietz ................ F02D 41/1476
                                                           204/401
5,112,296 A * 5/1992 Beard ................... A61F 5/0113
                                                           128/905
(Continued)

*Primary Examiner* — Justine R Yu
*Assistant Examiner* — Benjamin M. Kusiak
(74) *Attorney, Agent, or Firm* — Fish & Richardson P.C.

(57) ABSTRACT

The disclosure features adaptive sleeves that include a sensor, an electronic processor connected to the sensor, an adjustable voltage source connected to the electronic processor, and a sleeve formed of a fabric material and including one or more deformable elements attached to or embedded within the fabric material and connected to the adjustable voltage source, where during operation of the adaptive sleeve, the electronic processor is configured to apply a force to a portion of a body of a sleeve wearer in proximity to a contracted muscle in the wearer's body by receiving an input electrical signal from the sensor, and adjusting the voltage source to apply an output electrical signal to the one or more deformable elements, the output electrical signal having a magnitude that is correlated with a magnitude of the input electrical signal.

14 Claims, 13 Drawing Sheets

(51) Int. Cl.
*A61F 5/01* (2006.01)
*A61N 1/04* (2006.01)
*A61N 5/06* (2006.01)

(52) U.S. Cl.
CPC .......... *A61F 5/0109* (2013.01); *A61B 5/0053* (2013.01); *A61B 5/0059* (2013.01); *A61B 5/6824* (2013.01); *A61B 5/6828* (2013.01); *A61B 5/6829* (2013.01); *A61B 2560/0214* (2013.01); *A61F 2005/0155* (2013.01); *A61F 2005/0188* (2013.01); *A61N 1/0452* (2013.01); *A61N 2005/0645* (2013.01); *A61N 2005/0659* (2013.01)

(58) Field of Classification Search
CPC ..... A61F 2007/0042; A61F 2007/0071; A61N 1/0452; A63B 21/00076; A63B 23/0405; A41D 27/10
USPC ............ 601/84, 5, 33, 34, 87; 600/546, 554; 2/59, 125
See application file for complete search history.

(56) References Cited

U.S. PATENT DOCUMENTS

| | | | | |
|---|---|---|---|---|
| 5,927,060 | A * | 7/1999 | Watson | D02G 3/12 337/163 |
| 7,413,802 | B2 * | 8/2008 | Karayianni | D02G 3/328 428/370 |
| 7,926,254 | B2 * | 4/2011 | Karayianni | D02G 3/328 57/310 |
| 8,162,857 | B2 * | 4/2012 | Lanfermann | A41D 13/1281 600/595 |
| 8,517,963 | B2 * | 8/2013 | Larson | A61B 17/1325 602/13 |
| 2003/0125781 | A1 * | 7/2003 | Dohno | A63B 21/00181 607/75 |
| 2005/0282009 | A1 * | 12/2005 | Nusko | D02G 3/12 428/375 |
| 2008/0071386 | A1 * | 3/2008 | McBean | A61F 5/0127 623/25 |
| 2010/0275338 | A1 * | 11/2010 | Hyde | A61B 5/1077 2/69 |
| 2013/0085538 | A1 * | 4/2013 | Volpe | A61N 1/3975 607/6 |
| 2015/0152852 | A1 * | 6/2015 | Li | H02N 11/006 60/528 |
| 2015/0266180 | A1 * | 9/2015 | Kornbluh | B25J 9/0006 700/260 |
| 2015/0314123 | A1 * | 11/2015 | Sharma | A61N 1/08 607/116 |
| 2015/0366504 | A1 * | 12/2015 | Connor | A61B 5/6804 600/301 |
| 2016/0202755 | A1 * | 7/2016 | Connor | A61B 5/1126 73/865.4 |
| 2016/0220808 | A1 * | 8/2016 | Hyde | A61N 1/0452 |
| 2016/0324677 | A1 * | 11/2016 | Hyde | A61F 5/34 |
| 2016/0338644 | A1 * | 11/2016 | Connor | A61B 5/4528 |
| 2017/0202724 | A1 * | 7/2017 | De Rossi | A61H 3/00 |
| 2017/0274249 | A1 * | 9/2017 | Moebius | A63B 21/00845 |
| 2017/0360586 | A1 * | 12/2017 | Dempers | A61F 5/0109 |
| 2018/0008196 | A1 * | 1/2018 | Connor | A61B 5/6804 |
| 2018/0125425 | A1 * | 5/2018 | Garudadri | A61B 5/6828 |
| 2018/0289313 | A1 * | 10/2018 | Inan | A61B 5/4528 |

\* cited by examiner

Legend
110: power supply
202: MOSFET
213: adjustable voltage source

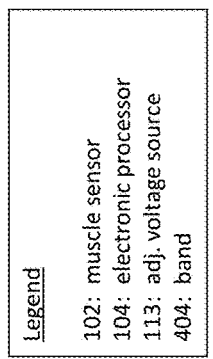
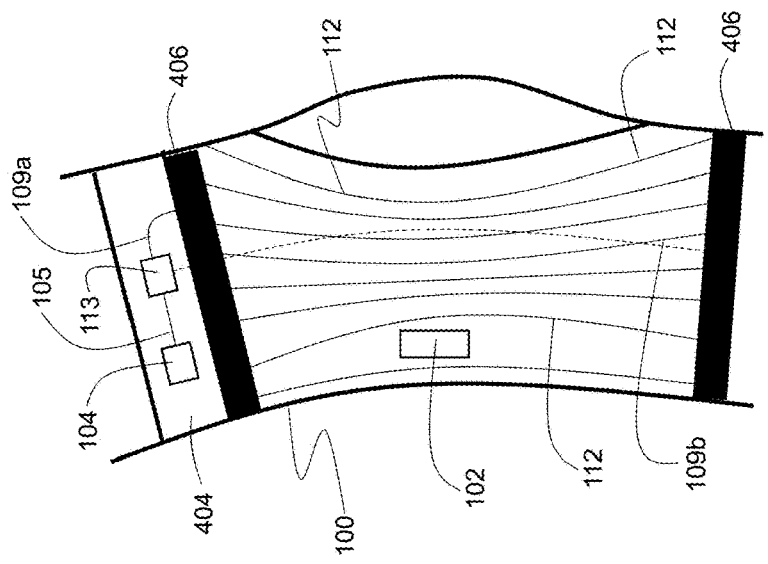
FIG. 5
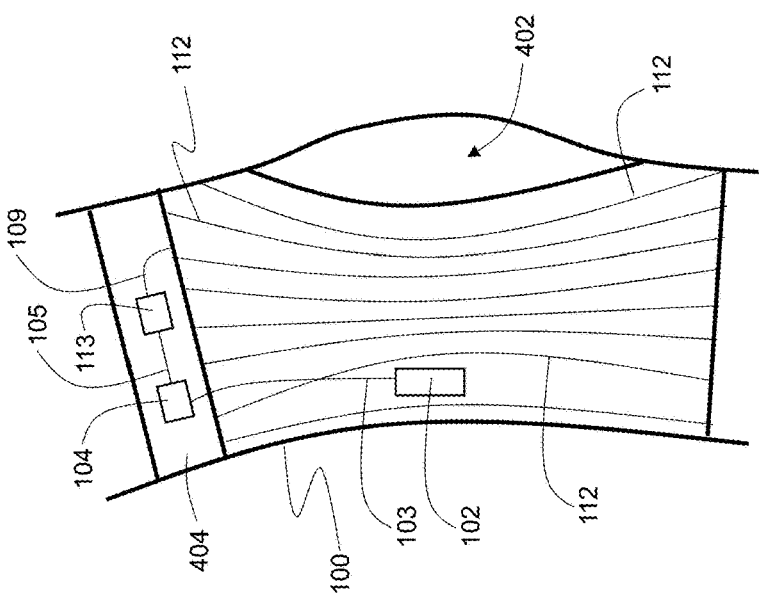
FIG. 4

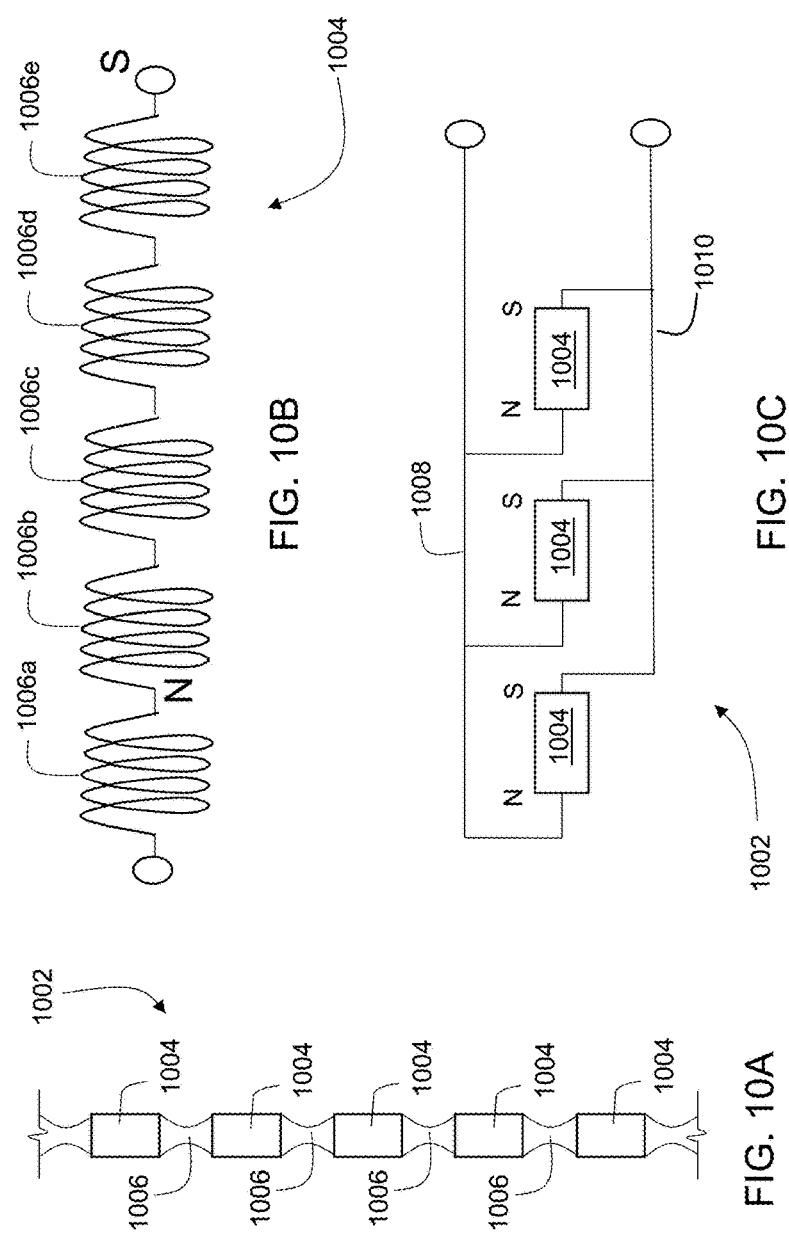

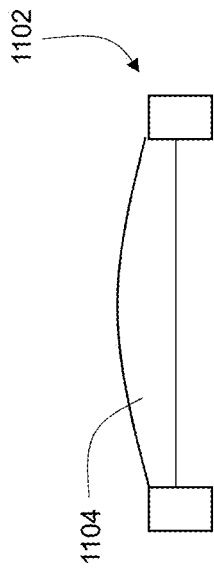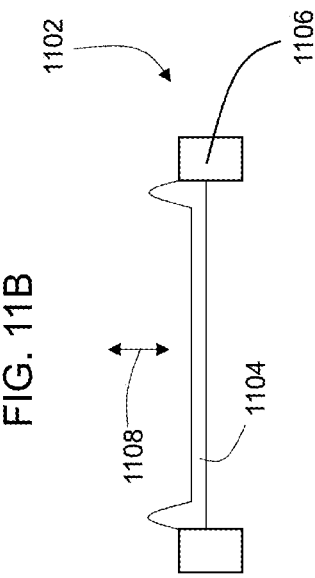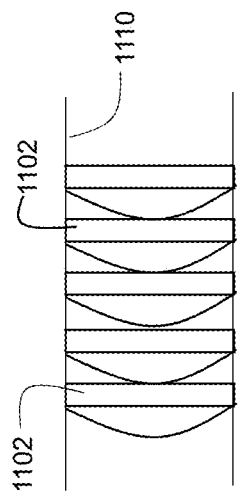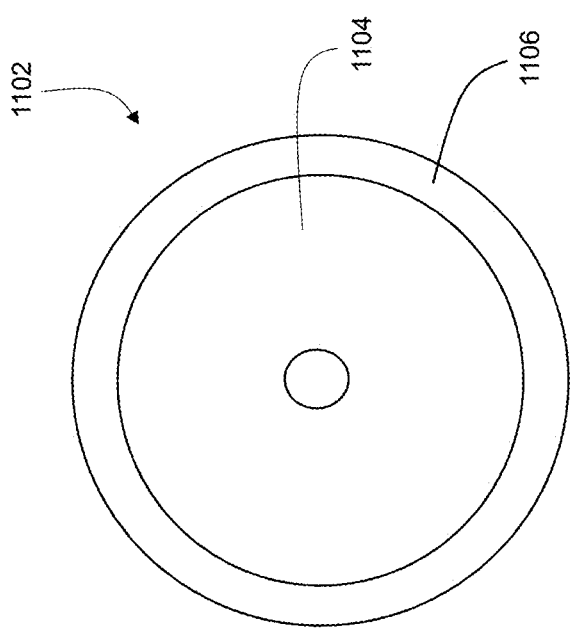

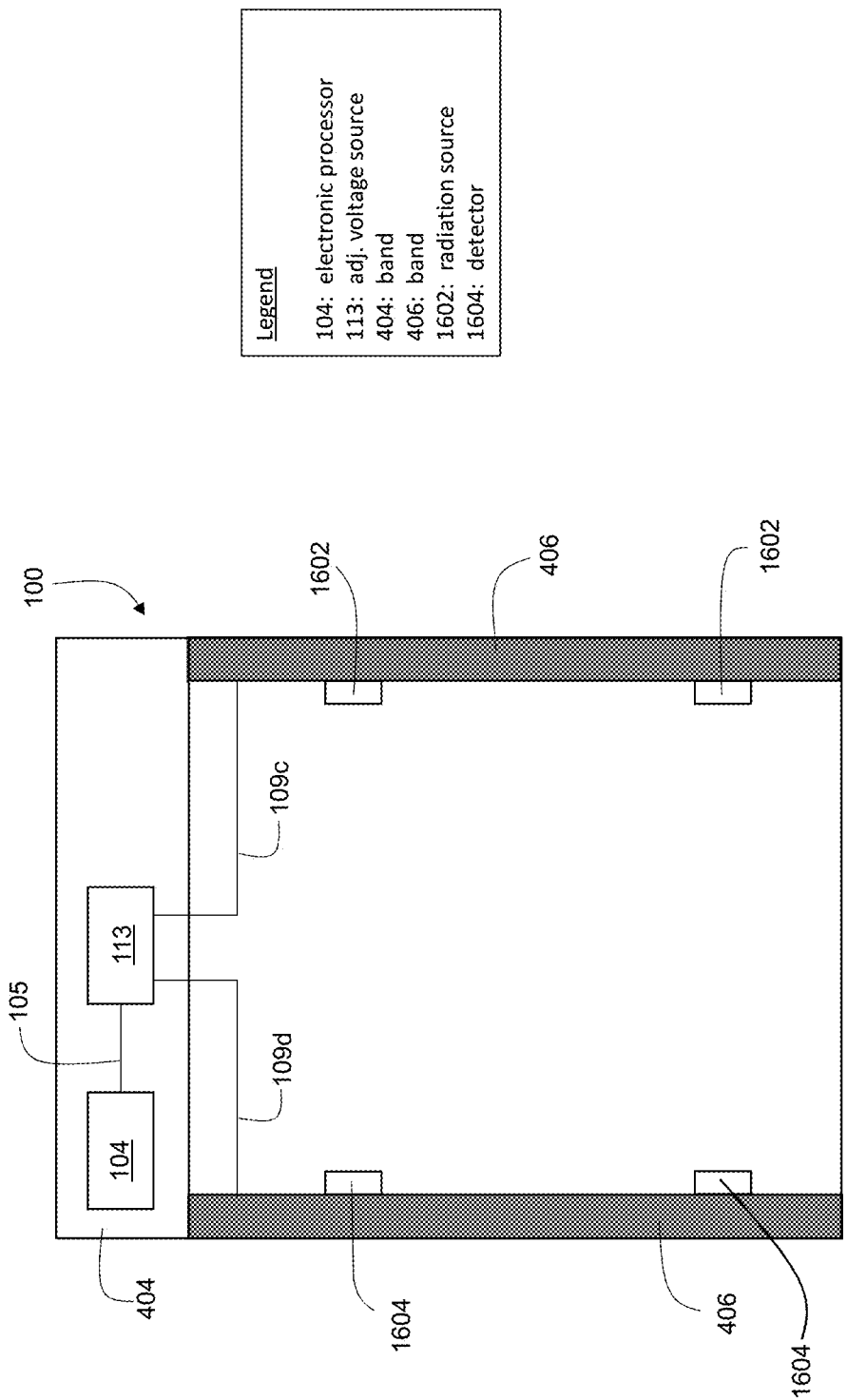

ADAPTIVE COMPRESSION SLEEVES AND CLOTHING ARTICLES

TECHNICAL FIELD

This disclosure relates to sleeves, braces, and articles of clothing that provide support for joints via active compression.

BACKGROUND

Conventional compression braces or sleeves are worn by athletes, patients, and elderly persons, all of whom benefit from supplementary joint support provided by such braces or sleeves. Braces or sleeves can be worn for extended periods of time, during periods of relative inactivity and also during periods of relatively vigorous physical activity.

SUMMARY

This disclosure features active sleeves that apply variable force to a portion of the wearer's body, according to an extent to which the wearer's muscles have contracted. The sleeves include a sensor that measures muscle contraction, and an electronic processor that receives the sensor signal and causes deformable elements in the sleeves to contract responsively. By operating in such an active manner, the sleeves apply force to the wearer's body only when appropriate. At other times, the sleeves remain in a relaxed state, allowing for improved blood flow and reduced pain within the wearer's body relative to conventional braces or sleeves. Deformable elements in the sleeves can be positioned so that they contract along the same direction as the wearer's muscles, thereby functioning as supplemental musculature and enhancing the wearer's mobility and natural muscular activities.

In general, the disclosure features adaptive sleeves that include a sensor configured to generate an electrical signal in response to contraction of a muscle, an electronic processor connected to the sensor, an adjustable voltage source connected to the electronic processor, and a sleeve formed of a fabric material and including one or more deformable elements attached to or embedded within the fabric material and connected to the adjustable voltage source, where during operation of the adaptive sleeve, the electronic processor is configured to apply a force to a portion of a body of a sleeve wearer in proximity to a contracted muscle in the wearer's body by receiving an input electrical signal from the sensor indicative of contraction of the muscle, and adjusting the voltage source to apply an output electrical signal to the one or more deformable elements, the output electrical signal having a magnitude that is correlated with a magnitude of the input electrical signal, and the applied output electrical signal causing the one or more deformable elements to deform, thereby applying the force to the portion of the body of the sleeve wearer.

Embodiments of the sleeves can include any one or more of the following features.

The adjustable voltage source can include a power supply, an adjustable servo motor, and a potentiometer. The adjustable voltage source can include a power supply and a MOSFET.

The one or more deformable elements can be positioned within the fabric material so that the electronic processor applies a compressive force to the portion of the body of the sleeve wearer. At least some of the one or more deformable elements can be aligned along a common direction within the fabric material. At least one portion of the fabric material can include no deformable elements and can be configured to be positioned over a joint in the body of the sleeve wearer.

At least some of the deformable elements can include a twisted filament formed of at least one polymer material. Each of the at least some of the deformable elements can include an electrically conductive wire wrapped around the twisted filament. The electrically conductive wire can form multiple pluralities of loops wrapped around the twisted filament, each of the multiple pluralities of loops being separated by a distance along a length of the twisted filament of at least twice a diameter (e.g., at least 5 times the diameter) of the electrically conductive wire.

At least some of the deformable elements can include a plurality of coils of conductive material mechanically and electrically connected together. At least some of the deformable elements can include a membrane, a first electrode formed on a first side of the membrane, and a second electrode formed on a second side of the membrane and opposite the first side, where the first and second electrodes are positioned so that when an electrical potential is applied between the first and second electrodes, a distance between the first and second electrodes along a first direction is reduced, and a portion of the membrane extends in a direction parallel to the first direction.

The deformable elements can be positioned within the fabric material so that when contraction of the muscle occurs along a first direction, the one or more deformable elements deform at least partially along the first direction.

The magnitude of the output electrical signal can be linearly proportional to the magnitude of the input electrical signal. The magnitude of the output electrical signal can be non-linearly correlated with the magnitude of the input electrical signal.

The output electrical signal can cause the one or more deformable elements to deform by resistively heating the one or more deformable elements.

The sleeves can include one or more electrodes connecting the one or more deformable elements to the adjustable voltage source, where the one or more electrodes include electrical conductors embedded within the fabric material.

The sensor can be a first sensor and the one or more deformable elements can be a first set of deformable elements, and the sleeves can include a second sensor connected to the electronic processor and configured to generate an electrical signal in response to contraction of a muscle, and a second set of one or more deformable elements attached to or embedded within the fabric material and connected to the adjustable voltage source, where during operation of the adaptive sleeves, the electronic processor can be configured to receive input electrical signals from the first and second sensors, determine which of the first and second sets of deformable elements to activate based on the input electrical signals, and adjust the voltage source to apply output electrical signals to one or both of the first and second sets of deformable elements, thereby applying the force to the portion of the body of the sleeve wearer.

At least some of the first set of deformable elements can correspond to a first type of deformable element, and at least some of the second set of deformable elements can correspond to a second type of deformable element different from the first type. The electronic processor can be configured to adjust the voltage source to apply different output electrical signals to the first and second sets of deformable elements, and magnitudes of the different output electrical signals can be correlated with magnitudes of the input electrical signals from the first and second sensors, respectively. At least some members of the first set of deformable elements can be aligned along a first direction in the sleeve, and at least some members of the second set of deformable elements can be aligned along a second direction in the sleeve that is different from the first direction.

Embodiments of the sleeves can also include any of the other features disclosed herein, including combinations of features disclosed in connection with different embodiments, in any combination as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 4 is a schematic diagram showing another example of an adaptive sleeve.

FIG. 5 is a schematic diagram showing a further example of an adaptive sleeve.

FIG. 10A is a schematic diagram showing an example of an electromagnetic actuator in an extended state.

FIG. 10B is a schematic diagram showing a portion of the electromagnetic actuator of FIG. 10A.

FIG. 10C is a schematic diagram showing electrical connections between portions of the electromagnetic actuator of FIG. 10A.

FIG. 10D is a schematic diagram showing the electromagnetic actuator of FIG. 10A in a contracted state.

FIG. 11A is a top view of an electroactive polymer-based actuator.

FIG. 11B is a cross-sectional view of the actuator of FIG. 11A in an un-activated state.

FIG. 11C is a cross-sectional view of the actuator of FIG. 11A in an activated state.

FIG. 11D is a side view of an actuator that includes multiple electroactive polymer-based actuators enclosed by a sheath.

FIG. 16 is a schematic diagram of an example of an adaptive sleeve that includes radiation sources and detectors.

Like reference symbols in the various drawings indicate like elements.

DETAILED DESCRIPTION

Conventional compression braces or sleeves are "static", applying constant force to the portion of the wearer's body over which they are positioned. Blood flow is typically restricted when force is applied by a compression brace or sleeve. Prolonged use of such sleeves can therefore result in extended constriction of blood flow within joints and limbs, an undesirable therapeutic outcome. Static compression over an extended period of time can also irritate sensitive nerves and even cause bruising of tissue, leading to chronic discomfort and pain. Unfortunately, users of conventional braces or sleeves who benefit from long-term support provided by such braces also experience these drawbacks.

The present disclosure features adaptive sleeves that exert force on a portion of the wearer's body when the application of force is appropriate (i.e., when the wearer's muscles contract), and that are otherwise maintained in a relaxed state when application of force is not appropriate. As such, the sleeves provide enhanced support for muscles and joints when such support is beneficial, and do not restrict blood flow or apply pain-inducing pressure when support is not required. The sleeves adaptively apply force to the wearer's body such that the magnitude of the force is related to the extent of compression of the wearer's muscles. As such, the sleeves respond dynamically to the wearer's musculature. In addition to applying compressive force to support joints and limbs, deformable elements in the sleeves can be aligned with the wearer's own muscles and can deform in the same direction as the wearer's muscles, thereby enhancing the wearer's muscular strength. Operation in this manner can improve the wearer's mobility and enhance the wearer's ability to execute other muscle-related movements and tasks.

System Overview

Figure 1:
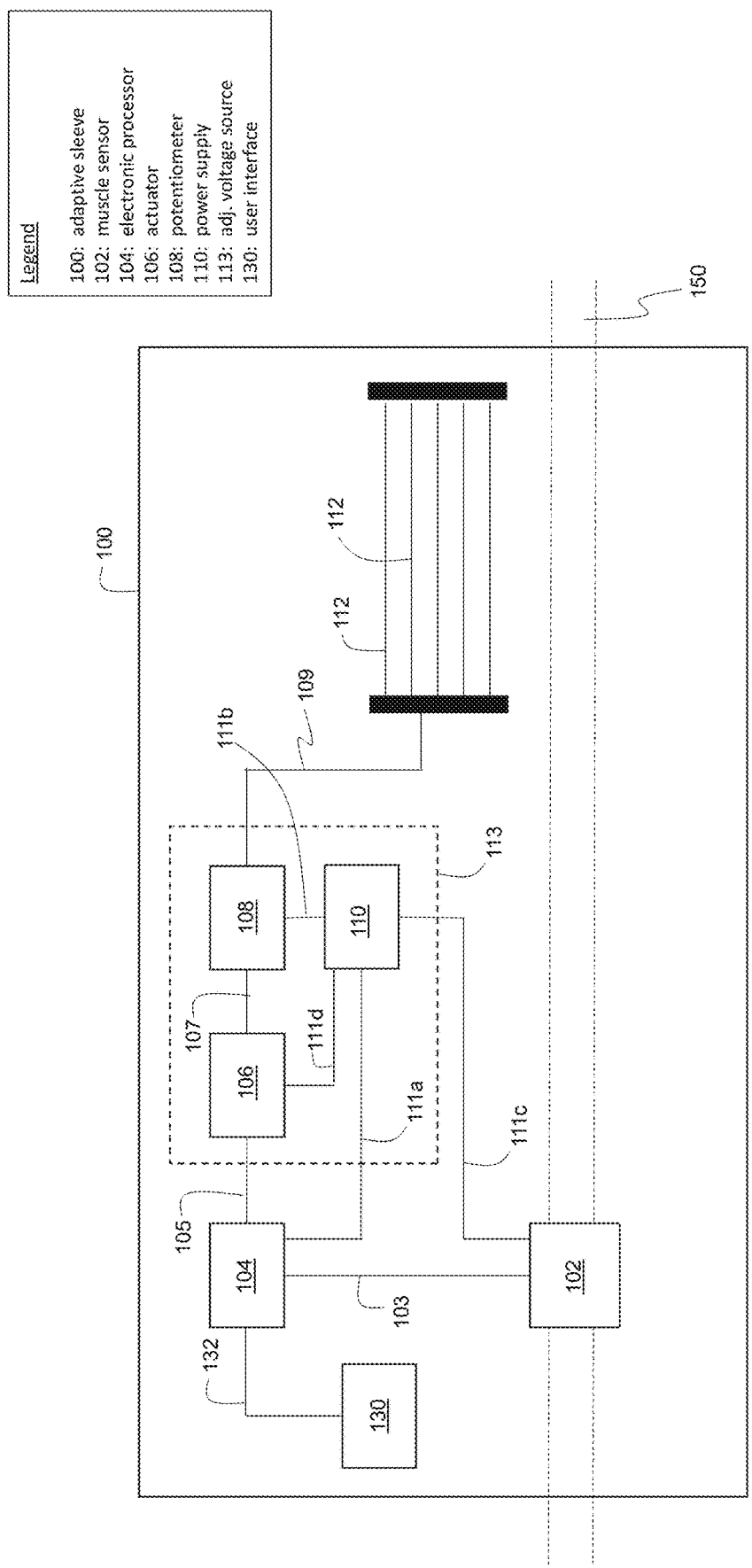
FIG. 1 is a schematic diagram showing an example of an adaptive sleeve.

FIG. 1 is a schematic diagram showing an embodiment of an adaptive sleeve 100. Sleeve 100 includes a muscle sensor 102 connected to an electronic processor 104 via control line 103, and to a power supply 110 via control line 111*c*. Electronic processor 104 is connected to an actuator 106 via control line 105, and to power supply 110 via control line 111*a*. Actuator 106 is connected to potentiometer 108 via control line 107 and to power supply 110 (e.g., a battery) via control line 111*d*. Potentiometer 108 is connected to one or more deformable elements 112 via control line 109. Together, actuator 106, potentiometer 108, and power supply 110 form an adjustable voltage source 113 which is controlled by electronic processor 104.

Muscle sensor 102 is positioned on or within sleeve 100 so that when sleeve 100 is worn, muscle sensor 102 is positioned adjacent or in proximity to a wearer's muscle. Flexure of the adjacent or proximal muscle by the wearer is detected by the muscle sensor 102 and used by the electronic processor 104 to adaptively adjust sleeve 100. An example of such a muscle 150 is shown in dashed lines in FIG. 1. When muscle 150 contracts, muscle sensor 102 generates an electrical signal in response to the contraction of muscle 150. The magnitude of the generated electrical signal depends on the extent of contraction of muscle 150; the greater the extent of contraction, the larger the magnitude of the signal generated by sensor 102.

Muscle sensor 102 can generally be implemented in a variety of ways. For example, in some embodiments, muscle sensor 102 can be an electromyographic sensor that detects a change in bio-electrical potential when muscle 150 contracts. Suitable electromyographic sensors can include, for example, the MyoWare Muscle Sensor, available from Advancer Technologies (Raleigh, N.C.). More generally, muscle sensor 102 can include any of a variety of devices that generate an electrical signal in response to contraction of muscle 150.

The electrical signal generated by muscle sensor 102 is received by electronic processor 104 as an input electrical signal. Electronic processor 104 is configured to generate an output electrical signal based on the input electrical signal. The output electrical signal causes deformable elements 112 in sleeve 100 to deform (e.g., to contract, to expand, or more generally, to change shape), thereby applying a force to the body of the wearer of sleeve 100. Depending upon the location of deformable elements 112 relative to muscle 150, the force can be applied directly to a portion of the wearer's body that includes muscle 150, or to tissue that is in proximity to muscle 150.

Electronic processor 104 generates the output signal by adjusting voltage source 113. In FIG. 1, voltage source 113 includes actuator 106, potentiometer 108, and power supply 110. To adjust voltage source 113 (i.e., to generate an output electrical signal corresponding to a particular voltage), electronic processor 104 generates a control signal that is transmitted to actuator 106 along control line 105. The control signal causes motion in actuator 106 by an amount that is related to a parameter of the control signal, such as voltage and/or current.

The motion of actuator 106 is coupled to potentiometer 108, either via electronic control line 107 or via a mechanical connection between actuator 106 and potentiometer 108. As a result, potentiometer 108 is adjusted according to the control signal generated by electronic processor 104. Power supply 110 generates a voltage signal that is transmitted to potentiometer 108 via control line 111b. Potentiometer 108—adjusted based on the control signal from electronic processor 104—modulates the voltage signal transmitted by power supply 110, generating an output electrical signal along control line 109 that is transmitted to deformable elements 112. In the foregoing manner, electronic processor 104 can effectively transmit an adjustable output electrical voltage signal to deformable elements 112.

Figure 2:
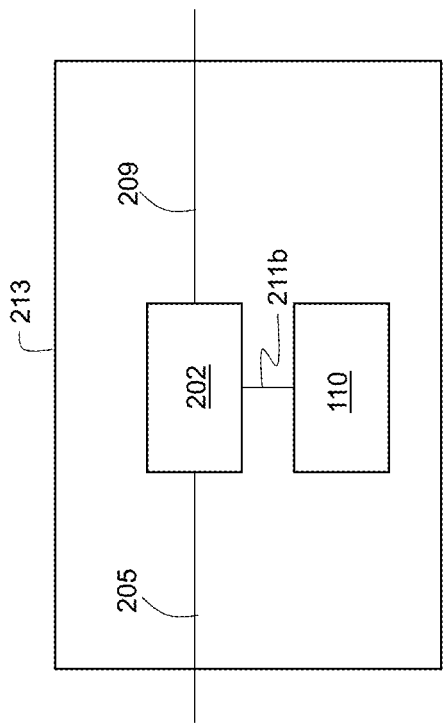
FIG. 2 is a schematic diagram showing an example of an adjustable voltage source.

As discussed above and shown in FIG. 1, in some embodiments, adjustable voltage source 113 includes an actuator, a potentiometer, and a power supply. More generally, any adjustable voltage source that can be adjusted by electronic processor 104 can be used in sleeve 100 to generate the output electrical signal that is transmitted to deformable elements 112. FIG. 2 shows a schematic diagram of another embodiment of an adjustable voltage source 213 that is based on a MOSFET 202. In voltage source 213, control line 205 delivers a gate voltage to MOSFET 202 from electronic processor 104, and control line 211b delivers a source voltage to MOSFET 202. The drain voltage, which corresponds to the output electrical signal, is transmitted from MOSFET 202 on control line 209, which is connected to deformable elements 112.

Returning to FIG. 1, in general, the magnitude of the output electrical signal generated by adjustable voltage source 113 under the control of electronic processor 104 is correlated with the magnitude of the input electrical signal received from muscle sensor 102. Deformable elements 112 are generally implemented such that the extent of deformation depends upon the magnitude of the output electrical signal. Moreover, muscle sensor 102 is configured so that the magnitude of the electrical signal it generates depends on the extent of contraction of muscle 50.

Thus, by correlating the magnitude of the output electrical signal with the magnitude of the input electrical signal, electronic processor 104 can adaptively adjust the amount of force that is applied to the body of a wearer of sleeve 100. For a relatively large muscle contraction, which may indicate a significant motion by the wearer, electronic processor 104 can cause deformable elements 112 to deform significantly, thereby applying a relatively large supporting force to the wearer's body. For a smaller muscle contraction, which may result from more limited motion by the wearer, electronic processor 104 can cause deformable elements 112 to deform less significantly, applying a more limited supporting force to the wearer's body.

The magnitudes of the input electrical signal and output electrical signal can be correlated according to various relationships. In some embodiments, for example, the magnitudes of the input and output electrical signals are linearly related, so that the magnitude of the output electrical signal varies in direct proportion to the magnitude of the input electrical signal. In certain embodiments, the magnitudes of the input and output electrical signals are non-linearly related. For example, the variation of the magnitude of the output electrical signal as a function of the magnitude of the input electrical signal can be described by a power law function or an exponential function, with the magnitude of the output electrical signal either growing or reaching an asymptotic limit as an exponential function or as a polynomial function of the magnitude of the input electrical signal.

Figure 3:
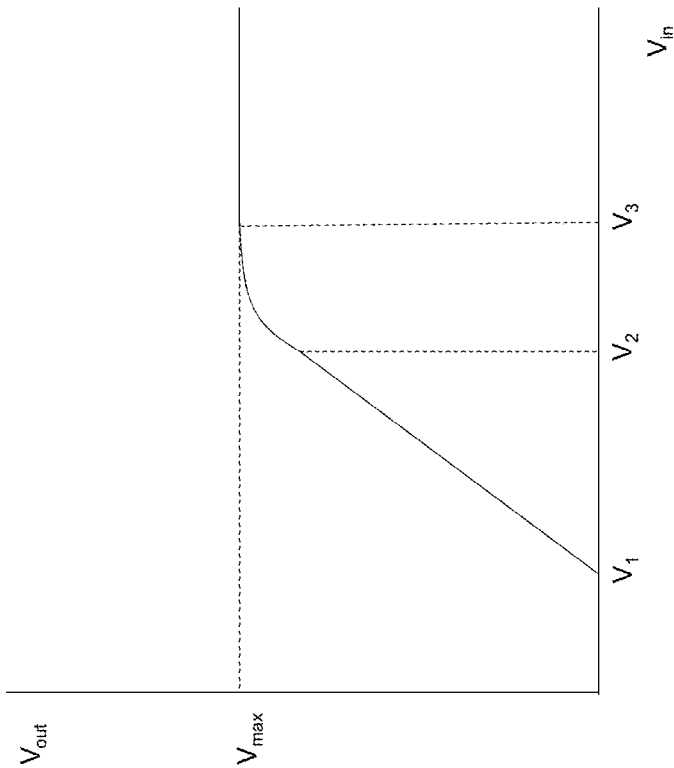
FIG. 3 is a plot showing an example of an output electrical signal as a function of an input electrical signal.

In some embodiments, electronic processor 104 is configured to implement a more complex scaling relationship between the magnitudes of the input and output electrical signals. One example of such a relationship is shown in FIG. 3, in which the magnitude of the output electrical signal, $V_{out}$, is plotted against the magnitude of the input electrical signal, $V_{in}$. In FIG. 3, for $V_{in} < V_1$, $V_{out} = 0$. $V_1$ represents a first threshold voltage below which electronic processor 104 does not generate an output electrical signal to drive deformable elements 112. By not generating an output electrical signal for relatively small input electrical signal magnitudes, electronic processor 104 effectively prevents sleeve 100 from responding to relatively small muscle contractions in the wearer's body. Such small contractions may correspond to small movements by the wearer that do not significantly benefit from auxiliary support provided by sleeve 100. These small muscle contractions may even be involuntary by the wearer, such that deformation by deformable elements 112 in response would be a nuisance.

For $V_1 < V_{in} < V_2$, $V_{out}$ is directly proportional to $V_{in}$, and may scale linearly or non-linearly with $V_{in}$ as discussed above, depending upon the desired rate at which sleeve 100 applies additional support to the wearer's body as muscle contraction occurs. $V_2$ represents a second threshold voltage that marks the end of this "high responsiveness" region of the output electrical signal generated by electronic processor 104, in which processor 104 generates an output electrical signal having a magnitude (i.e., a voltage magnitude) that is strongly related to the magnitude of the input electrical signal, $V_{in}$.

For $V_2 < V_{in} < V_3$, $V_{out}$ increases as a function of $V_{in}$, but at a rate that is smaller than between $V_1$ and $V_2$. In this region, the magnitude of the output signal, $V_{out}$, effectively saturates as $V_{in}$ increases toward $V_3$. $V_{out}$ is typically a nonlinear function of $V_{in}$, and can, for example, be a polynomial or exponential function of $V_{in}$ in this region. The region from $V_2$ to $V_3$ can represent a "saturation" region of the output electrical signal generated by electronic processor 104.

$V_{out}$ saturates for $V_{in} > V_3$, so that $V_{out}$ does not exceed $V_{max}$. $V_3$ can be regarded as a third threshold voltage that corresponds to an output limit for electronic processor 104. Input electrical signals having magnitudes larger than $V_3$ still generate an output electrical signal having a magnitude of $V_{max}$. In some embodiments, $V_3$ effectively functions as a safety limit, ensuring that sleeve 100 does not excessively compress or apply force to the wearer's body.

In FIG. 3, $V_{out}$ approaches the value $V_{max}$ asymptotically between $V_2$ and $V_3$. In general, other functional forms describing the relationship between $V_{out}$ and $V_{in}$ are also possible between $V_2$ and $V_3$. In some embodiments, for example, $V_{out}$ depends linearly on $V_{in}$, but the slope of the output electrical signal response curve in FIG. 3 is smaller than the slope between $V_1$ and $V_2$. In certain embodiments, $V_{out}$ does not approach $V_{max}$ asymptotically between $V_2$ and $V_3$, and instead the slope of the output electrical signal response curve in FIG. 3 is positive at $V_3$. Because $V_3$ functions as a threshold value, there is a discontinuity in the first derivative of the output electrical signal response curve at $V_3$, since $V_{out} = V_{max}$ for all $V_{in} > V_3$.

As discussed above, voltage source 113 typically includes a battery to provide operating power for electronic processor 104, muscle sensor 102, and for the other components of sleeve 100. In some embodiments, the battery is a single-use battery that is discarded when depleted. In certain embodiments, the battery is a rechargeable battery that can be recharged by connection to an AC or DC external power source. In some embodiments, sleeve 100 includes a kinetic charger coupled to the battery and configured to provide charging power to the battery when the wearer of sleeve 100 is in motion. Kinetic charging of the battery can extend the period of use of sleeve 100 before connection to an external power source becomes necessary.

Sleeve Structure

As discussed above, in general sleeve 100 includes a plurality of deformable elements 112 connected via one or more control lines 109 to electronic processor 104, which generates output electrical signals that activate the deformable elements 112 to apply force to the body of the sleeve wearer. In general, deformable elements 112 are oriented in sleeve 100 along directions that correspond to muscles underlying the tissue over which sleeve 100 is worn. FIG. 4 shows a schematic diagram of one example of sleeve 100. Sleeve 100 in FIG. 4 is intended to be worn over a joint of a patient (e.g., a knee), and includes an opening 402 that is positioned over the wearer's joint, so that flexural motion of the joint is not impeded. As shown in FIG. 4, deformable elements 112 (only some of which are labeled, for clarity) are typically oriented along a common longitudinal direction within sleeve 100, approximately along the length of the wearer's leg, and parallel to certain leg muscles within the wearer's lower thigh and upper calf.

Sleeve 100 also includes a band 404 along one edge of the sleeve to which electronic processor 104 and voltage source 113 are mounted. Further, muscle sensor 102 is affixed to sleeve 100 at a suitable position for sensing contractions in the wearer's muscles.

As discussed above, electronic processor 104 and voltage source 113 are connected via control line 105, and voltage source 113 is connected to deformable elements 112 via control line 109. Electronic processor 104 can selectively activate one, several, or all of deformable elements 112 within sleeve 100.

Sleeve 100 can be formed from a variety of materials. For example, in some embodiments, sleeve 100 is formed from one or more fabric materials including cotton, polyester, rayon, nylon, spandex, and wool. Such materials generally are electrically non-conductive and permit electrical isolation of each of deformable elements 112. In certain embodiments, sleeve 100 can be formed from one or more metallic materials, e.g., implemented as metallic threads, fibers, or mesh. Suitable metallic materials include, but are not limited to, copper, silver, aluminum, stainless steel, nickel, and metallic alloys. Such materials are generally electrically conductive, and can be used to electrically couple multiple deformable elements 112 so that an electrical control signal delivered from electronic processor 104 can be used to activate each of the coupled deformable elements 112.

In some embodiments, sleeve 100 can be formed from both non-conductive and conductive materials. For example, sleeve 100 can include a sleeve body formed of one or more strips or sections of non-conductive fabric (e.g., any of the non-conductive materials discussed above), and one or more pockets, connectors, electrodes, or other structures formed of one or more conductive materials (e.g., any of the conductive materials discussed above).

Deformable elements 112 can be attached to or incorporated within sleeve 100 in a wide variety of ways. In some embodiments, for example, deformable elements 112 can be woven into the fabric of sleeve 100 such that deformable elements 112 are interwoven with non-conductive and/or conductive materials within sleeve 100. In certain embodiments, deformable elements 112 are positioned in pockets formed within sleeve 100, with one or more deformable elements 112 in each pocket.

In some embodiments, deformable elements 112 are positioned between layers of sleeve 100. For example, sleeve 100 can include a first layer of one or more materials and a second layer of one or more materials (different or the same as the materials that form the first layer). Deformable elements 112 can be positioned interstitially between the two layers. More complex structures can also be employed. For example, sleeve 100 can include three or more layers, with groups of deformable elements 112 positioned between pairs of layers. Deformable elements 112 can also penetrate through layers so that one or more such elements extend between the interstitial spaces formed between different pairs of layers. Deformable elements 112 can be aligned along a common direction within each interstitial space, or alternatively, some deformable elements 112 can be aligned along different directions within a particular space between layers of sleeve 100. In certain embodiments, a first set of deformable elements 112 are aligned approximately parallel to one another along a first direction in a space between first and second layers of a sleeve 100, and a second set of deformable elements 112 are aligned approximately parallel to one another along a second direction in a space between second and third layers of sleeve 100, where the first and second directions are different. The differing orientations of the deformable elements 112 in the two spaces permits sleeve 100 to apply forces along different directions, as will be discussed in more detail below.

FIG. 5 is a schematic diagram showing another example of a sleeve 100 that includes electrode bands 406 connected to deformable elements 112 (only two of which are shown, for clarity). Bands 406 are formed of a conductive material (e.g., threads or fibers of one or more metallic materials) and are woven into, bonded to, or otherwise secured to the body of sleeve 100, which is formed from a non-conductive material. Each of deformable elements 112 extends between electrode bands 406, and each electrode band 406 is connected to voltage source 113 via one of control lines 109*a* and 109*b*. During operation, electronic processor 104 delivers an output electrical signal to electrode bands 406, activating deformable elements 112. The mode of activation of deformable elements 112 can include direct electrical activation (e.g., deformable elements 112 are activated directly by the electrical signal from electronic processor 104), resistive heating (e.g., deformable elements 112 change shape in response to resistive heating due to the electrical signal from electronic processor 104), or another mechanism. Examples of deformable elements 112 and their modes of activation are discussed below.

Figure 6:
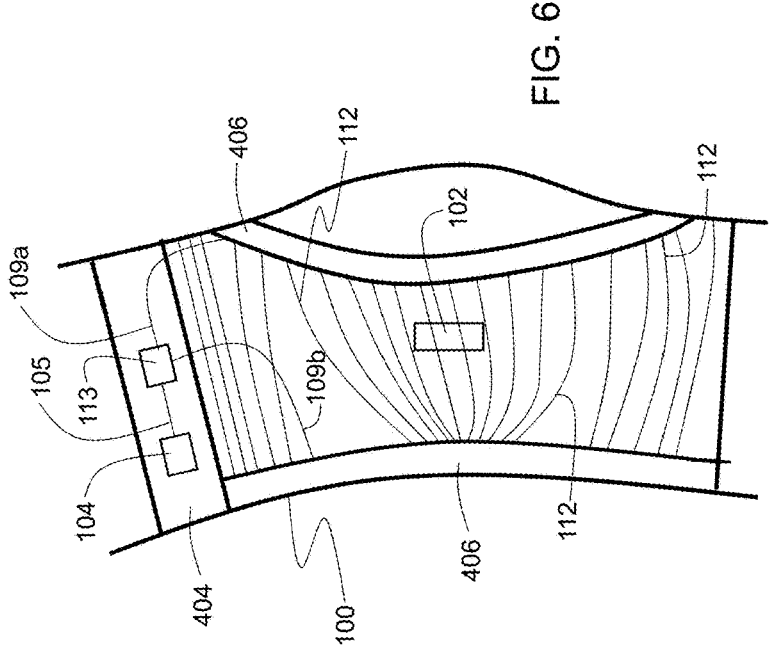
FIG. 6 is a schematic diagram showing another example of an adaptive sleeve.

FIG. 6 shows a schematic diagram of another example of a sleeve 100. Sleeve 100 in FIG. 6 includes an opening 402 and two electrode bands 406. Deformable elements 112 in FIG. 6 are oriented in a lateral direction in sleeve 100, approximately orthogonal to the orientation of deformable elements 112 in FIG. 4. When activated by electronic processor 104, deformable elements 112 in FIG. 6 deform laterally, thereby exerting a compressive force to the portion of the wearer's body on which sleeve 100 is positioned.

In some embodiments, as shown in FIGS. 4-6, sleeve 100 can be approximately tubular in shape and dimensioned to be worn over various portions of a wearer's body, including but not limited to knees, elbows, shoulders, ankles, and wrists. More generally, sleeve 100 can have a variety of shapes depending upon the shape of the portion of the body over which the sleeve is worn. Sleeve 100 can also include one or more straps, belts, clips, or other fastening mechanisms to secure the sleeve to the wearer's body.

Deformable Elements

A variety of different deformable elements can be used in sleeve 100 to apply force (e.g., compressive force) to the wearer's body. As discussed above, the deformable elements used can be activated in a variety of ways. Certain elements, for example, are activated by heating and deform in response to a change in temperature. Some elements are activated electrically, i.e., by an applied voltage and/or current, and deform in response to the applied electrical signal.

(a) Coiled Polymers

Figure 7A:
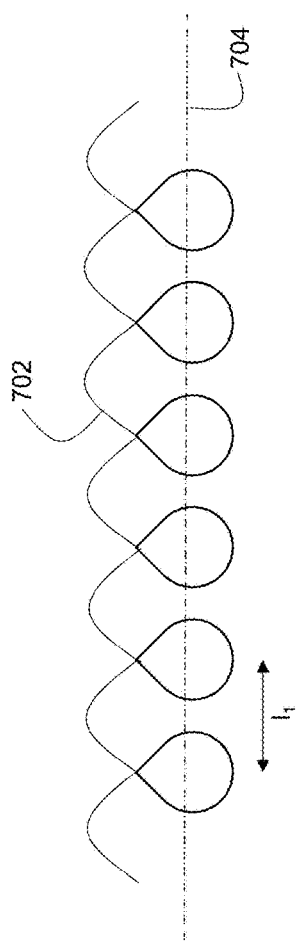
FIG. 7A is a schematic diagram showing an example of a coiled polymer-based actuator in an extended state.

In certain embodiments, deformable elements 112 in sleeve 100 can be implemented as coiled polymer strands. In general, the strands include helical loops formed of a polymer material, extending along a helical axis. At relatively lower temperature, the coiled polymer strands exist in an extended state along the helical axis, with adjacent loops spaced a relatively larger distance from one another along the axis. FIG. 7A shows a schematic diagram of a coiled polymer strand 702 that includes a plurality of helical loops extending along axis 704. The spacing between adjacent loops along axis 704 is $l_1$.

Figure 7B:
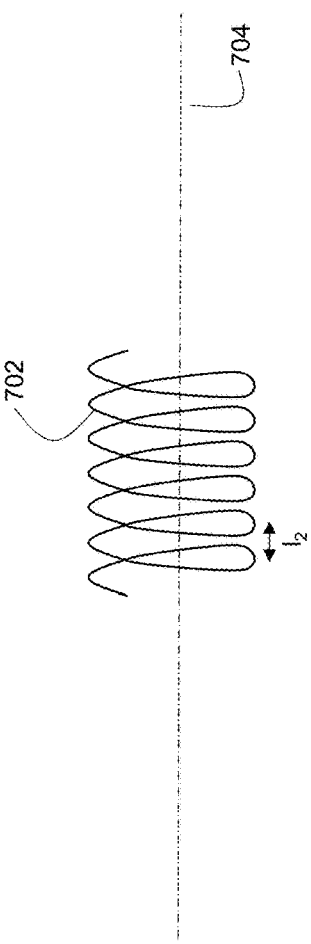
FIG. 7B is a schematic diagram showing an example of a coiled polymer-based actuator in a contracted state.

When the temperature of strand 702 is increased (e.g., by resistive heating), adjacent loops are drawn closer together along axis 704, as shown in FIG. 7B. The spacing between adjacent loops along axis 704 at higher temperature is $l_2$, which is smaller than $l_1$. The coiled polymer strands are implemented such that, when heat is applied to a strand, the strand attempts to expand and untwist—or unwind—its coiled loops. Because of the orientation of the loops, this attempt to untwist leads to a contraction of the length of the strand along axis 704, thereby applying force to the wearer's body.

To fabricate suitable coiled polymer strands for use as deformable elements 112, a monofilament thread formed from one or more polymers, such as nylon, polypropylene, polyethylene, was attached at a first end to a mass (e.g., approximately 170 g) and at a second end to a device such as a motor that can rotate the thread about its axis. The first end of the thread attached to the mass was secured so that it could not rotate. Then, the device attached to the second end was activated to rotate the thread about its axis, introducing helical loops into the thread structure. Rotation of the thread was continued until the helical loops extended along the entire axis of the thread. Initially, as loops were introduced via rotation along the axis of the thread, the loops merely increased the torsion along the length of the thread. However, as rotation continued, successive loops "flipped" their orientation along the thread, forming a tightly packed grouping of loops extending along the axis of the thread. These flipped loops were responsible for the constrictive motion of the thread upon heating.

After rotation of the thread was complete, the thread was further stretched by increasing the mass attached to the first end. Typically, the attached mass was increased by about 50%, causing axial elongation of the coiled thread.

The coiled thread was then heated to impart shape memory to the thread. Heating can generally be performed in a variety of ways. To fabricate the coiled polymer strands used herein, the coiled thread was wrapped with conductive material (e.g., a conductive filament) and the conductive filament was connected to a variable power supply. Once activated, the variable power supply directed an electrical current to flow through the conductive filament, causing resistive heating of the filament. The heat generated was thereby applied directly to the coiled thread. After a period of heating, the power supply was deactivated and the coiled thread was allowed to cool to room temperature.

This process of heating and cooling was repeated for multiple cycles for each coiled thread. For the first few cycles, the coiled thread elongated along the axial direction when heated and then returned to its original length when cooled. After these first cycles, however, application of heat to the coiled thread caused contraction of the thread, and the coiled thread was capable of lifting an attached mass. During each heating and cooling cycle, heating was continued until expansion or contraction along the axial direction stopped, and cooling continued until the reverse contraction or expansion along the axial direction stopped. The heating and cooling cycles were continued for each coiled thread until it was observed that each thread contracted along the axial direction upon heating, and then returned to a consistent elongated length upon cooling. Coiled threads fabricated in the above manner do not untwist upon cooling due to the cyclic heat treatment performed.

To implement coiled threads 702 as deformable elements 112 in sleeve 100, one or more heating elements can be used in sleeve 100 to increase the temperature of coiled threads 702, thereby causing contraction of the threads along their respective axial directions. Heating elements can be implemented in various ways. In some embodiments, for example, heating elements formed as threads or strips of conductive material can be woven into or affixed to the fabric material forming the body of sleeve 100. When activated by electronic processor 104, such heating elements generate heat resistively, thereby increasing the temperature of the coiled threads.

Figure 8:
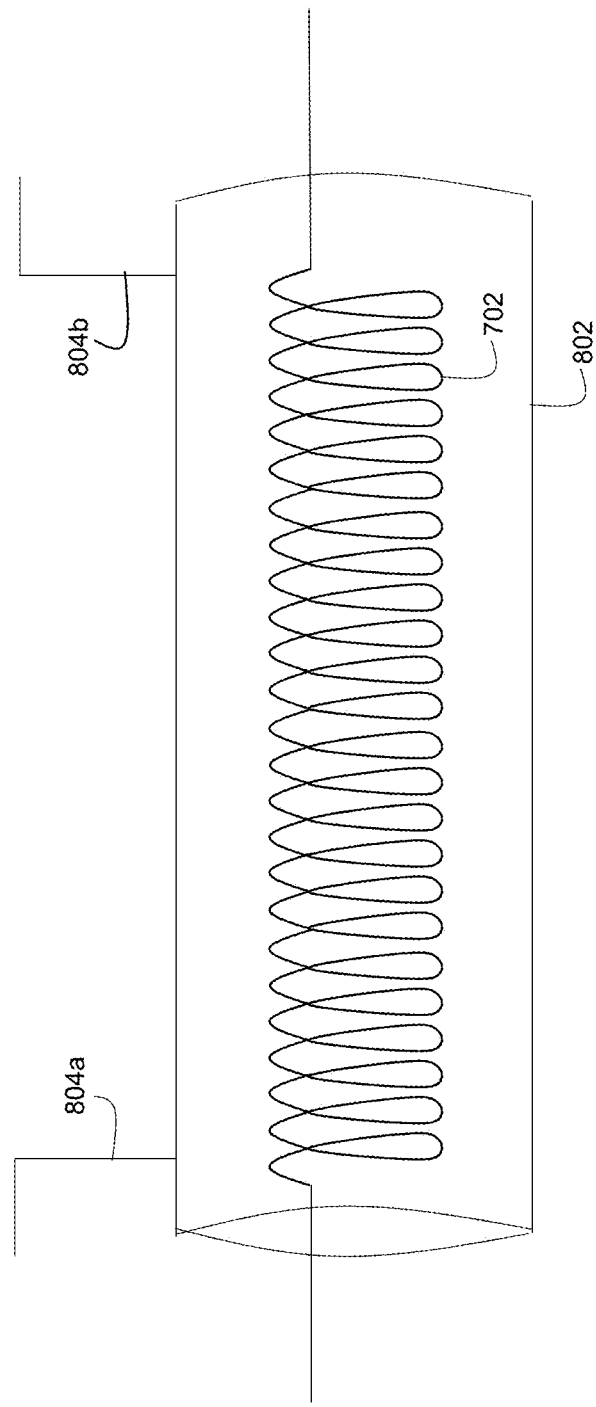
FIG. 8 is a schematic diagram showing an example of a coiled polymer-based actuator enclosed within a sleeve pocket.

In certain embodiments, coiled threads 702 can be enclosed within pockets formed in sleeve 100 from conductive materials such as metallic fabrics and/or metallic threads. FIG. 8 is a schematic diagram showing an example of a pocket 802 formed from a conductive material and featuring electrodes 804a and 804b which are connected to electronic processor 104 via one or more control lines 109. As shown in FIG. 8, coiled thread 702 is positioned within pocket 802. During operation, electronic processor 104 generates an output electrical signal, causing resistive heating of pocket 802. Heat generated by pocket 802 is thereby conducted to coiled thread 702, causing contraction of thread 702 along its axial direction as the temperature of thread 702 increases.

Figure 9:
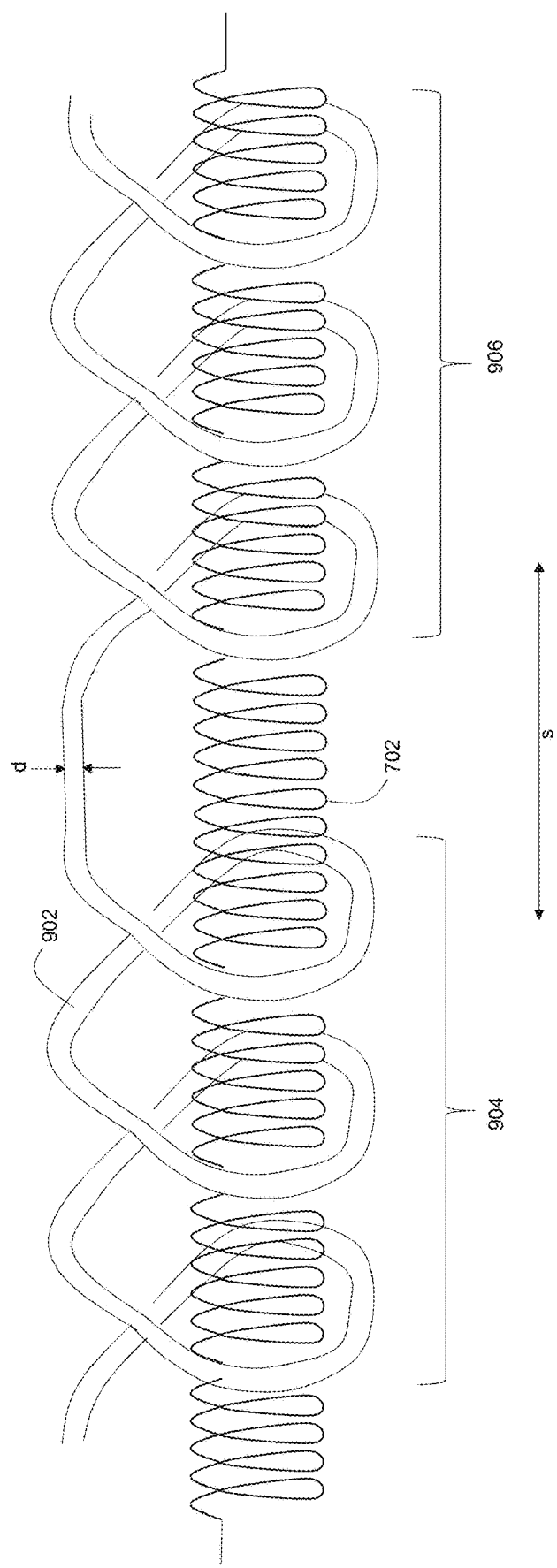
FIG. 9 is a schematic diagram showing an example of a coiled polymer-based actuator encircled by a conductive element.

In some embodiments, conductive elements encircle coiled threads 702 within the body of sleeve 100. Activation of the conductive elements by electronic processor 104 (i.e., via an output electrical signal generated by the electronic processor) causes resistive heating of the conductive elements, and the heat generated causes coiled threads 702 to contract along their axial directions. FIG. 9 is a schematic diagram showing an example of a coiled thread 702 within a sleeve 100. Encircling coiled thread 702 is a conductive element 902 (e.g., an electrically conductive wire). The ends of element 902 are in electrical communication with electronic processor 104 (e.g., via bands 406 and communication lines 109).

In certain embodiments, conductive element 902 includes a plurality of loops that extend along the entire length of coiled thread 702, so that when conductive element 902 is activated by electronic processor 104, heat is delivered approximately uniformly along the axial length of coiled thread 702. In some embodiments, however, conductive element 902 includes loops that encircle only portions of coiled thread 702, as shown in FIG. 9. As a result, heat is preferentially delivered to selected portions of thread 702 when conductive element 902 is activated. It has been observed that certain implementations of the structure shown in FIG. 9 are particularly efficient at causing contraction of coiled thread 702, and therefore, at applying a force to the wearer's body.

In FIG. 9, conductive element 902 includes a first plurality of loops 904 and a second plurality of loops 906, separated by a distance s. A thickness of conductive element 902 (i.e., a diameter of the electrically conductive wire that forms conductive element 902) is d. In some embodiments, activation of coiled thread 702 to apply a force to the wearer's body is particularly efficient when s is at least twice as large as d (e.g., at least 2.5 times as large as d, at least 3.0 times as large as d, at least 4.0 times as large as d, at least 5.0 times as large as d, at least 7.0 times as large as d).

Although conductive element 902 includes only two pluralities of loops 904 and 906 in FIG. 9, more generally conductive element 902 can include more than two pluralities of loops (e.g., three or more, four or more, five or more, six or more, eight or more, ten or more). Each plurality of loops can include the same number of loops, or certain pluralities of loops can have different numbers of loops. In general, each plurality or group of loops can include one or more loops (e.g., two or more loops, three or more loops, four or more loops, five or more loops, ten or more loops).

Pluralities or groups of loops with different numbers of loops can be used, for example, to control the manner in which contraction occurs along the axial length of coiled thread 702. Where conductive element 902 includes more than two pluralities of loops, similar considerations apply regarding the spacings s between adjacent pluralities of loops relative to the thickness d. In some embodiments, the spacings s between adjacent pluralities of loops are the same along the axial length of coiled thread 702. However, in certain embodiments, the spacings s between adjacent pluralities of loops can differ, allowing for further control over the manner in which contraction occurs along the axial length of coiled thread 702.

In certain embodiments, conductive materials can be coated directly on coiled threads 702 to permit heating of the threads. For example, once a coiled thread is fabricated as discussed above, the thread can be sprayed, dipped, or painted with one or more conductive materials (e.g., a paint or solution that includes metal particles such as silver, copper, gold, or aluminum), forming a coating of conductive material on a portion (or even the entire exterior surface) of the thread. The coated thread can be electrically connected to electronic processor 104 so that when processor 104 generates an output electrical signal, resistive heating of the coated thread 702 causes contraction along the axial direction of the thread as the temperature increases.

(b) Electromagnetic Actuators

In some embodiments, deformable elements 112 can be implemented as electromagnetic actuators. FIG. 10A is a schematic diagram showing an example electromagnetic actuator 1002. Actuator 1002 includes coil groups 1004 mechanically connected by a flexible membrane 1006. Flexible member 1006 can be formed, for example, from a variety of flexible, non-conductive polymer materials, rubber materials, silicone-based materials, and more generally, any mechanically compliant material that can be deformed.

Each coil group 1004 can be implemented in a variety of ways. FIG. 10B is a schematic diagram showing one example of a coil group 1004 that includes 5 helical coils 1006a-e electrically connected in series. In general, the number of coils in each group can be selected as desired, and each coil group 1004 can include one or more coils (e.g., two or more coils, three or more coils, five or more coils, seven or more coils, ten or more coils). Because the coils are connected in series and the loops of each coil are wound in a common direction, current flows through each coil in the group in the same helical direction. Thus, each coil group 1004 can be regarded as having a north pole at one end of the group and a south pole at the other end of the group as shown in FIG. 10B.

FIG. 10C is a schematic diagram showing electrical connections among coil groups 1004 of actuator 1002. As shown in FIG. 10C, each of the coil groups 1004 is connected in parallel to electrodes 1008 and 1010, and corresponding terminals of each coil group 1004 are connected to the same actuator, so that the loops of each coil in each group are wound in a common helical direction. As a result, the terminals of each of the coil groups 1004 corresponding to one of the poles are each connected to electrode 1008, and the terminals of each of the coil groups 1004 corresponding to the other of the poles are connected to electrode 1010.

When no potential difference is applied between the terminals of electrodes 1008 and 1010 by electronic processor 104, no current flows through the coil groups 1004. Actuator 1002 is therefore in the relaxed or extended state shown in FIG. 10A. However, when electronic processor 104 applies a voltage difference across the terminals of electrodes 1008 and 1010, an electrical current flows through each of the coil groups 1004, establishing magnetic poles for each coil group 1004. One example of the magnetic poles is shown in FIG. 10C. Because N and S poles for adjacent coil groups 1004 are opposite each other, adjacent coil groups experience an attractive force, and are drawn together. Flexible membrane 1006 deforms in response to the attractive force, allowing the adjacent coil groups to move toward each other, effectively resulting in contraction of actuator 1002. FIG. 10D is a schematic diagram showing actuator 1002 in a contracted state after activation by electronic processor 104.

In some embodiments, multiple actuators 1002 can be bundled together so that once activated, the multiple actuators contract cooperatively to apply larger forces to the wearer's body. For example, due to their relatively large aspect ratio, actuators 1002 can resemble threads which can be interwoven to form a mesh or a rope-like bundle of actuators. In certain embodiments, a portion of the body of sleeve 100 can be formed from such a mesh.

(c) Polymer Membrane-Based Actuators

In some embodiments, deformable elements 112 can be implemented as polymer membrane-based actuators. FIG. 11A is a schematic diagram showing an example of a polymer membrane-based actuator 1102. Actuator 1102 includes a membrane 1104 affixed to a frame 1106. Membrane 1104 is formed from one or more polymer materials such as, but not limited to, silicone-based polymers (e.g., polydimethylsiloxane) and rubber. Each surface of membrane 1104—the upper surface shown in FIG. 11A and the lower surface (not shown)—is coated with an electrically conductive material, so that each surface of membrane 1104 corresponds to an electrode. Suitable coating materials include, but are not limited to, carbon nanotubes, graphene, metallic nanoclusters, and patterned metal films.

The electrode surfaces of membrane 1104 are electrically isolated from one another by the thickness of the membrane material, and the electrode surfaces are connected to electronic processor 104 via bands 406 and control lines 109. FIG. 11B shows a cross-sectional schematic diagram of actuator in its relaxed, or un-activated, state. In FIG. 11B, no voltage difference is applied between the electrode surfaces of membrane 1104.

To activate actuator 1102, electronic processor 104 generates an output electrical signal that is applied as a voltage difference between the electrode surfaces of membrane 1104. In response to the applied voltage difference, the two membrane surfaces are drawn closer together due to the voltage difference and the compliant nature of membrane 1104. The squeezing of membrane 1104 between the electrodes causes expansion of membrane 1104 toward the edges of the membrane. FIG. 11C shows a schematic diagram of actuator 1102 following activation. In FIG. 11C, the thickness of membrane 1104 between the upper and lower surfaces is reduced (i.e., along direction 1108) as membrane 1104 is squeezed between the upper and lower surfaces. As a result, the edges of membrane 1104 extend upwards (i.e., in a direction parallel to direction 1108).

As a result, actuator 1102 can be used for applications in which deformable elements 112 contract upon activation, and for applications in which deformable elements 112 expand upon activation. In certain embodiments, multiple actuators 1102 can be stacked together and surrounded by a sheath 1110, as shown in the schematic diagram of FIG. 11D, to form a composite actuator. Each of the actuators 1102 can be activated in parallel within such a composite actuator to increase the range of compression and/or expansion relative to a single actuator 1102.

Sensor Configurations

In FIG. 4, sleeve 100 includes a muscle sensor 102 affixed at a location in sleeve 100 such that muscle sensor 102 senses contraction of a wearer's muscle or muscle group, thereby providing a feedback signal to electronic processor 104. In general, muscle sensor 102 can be positioned at any location in sleeve 100 to provide a measurement signal for processor 104.

Figure 12:
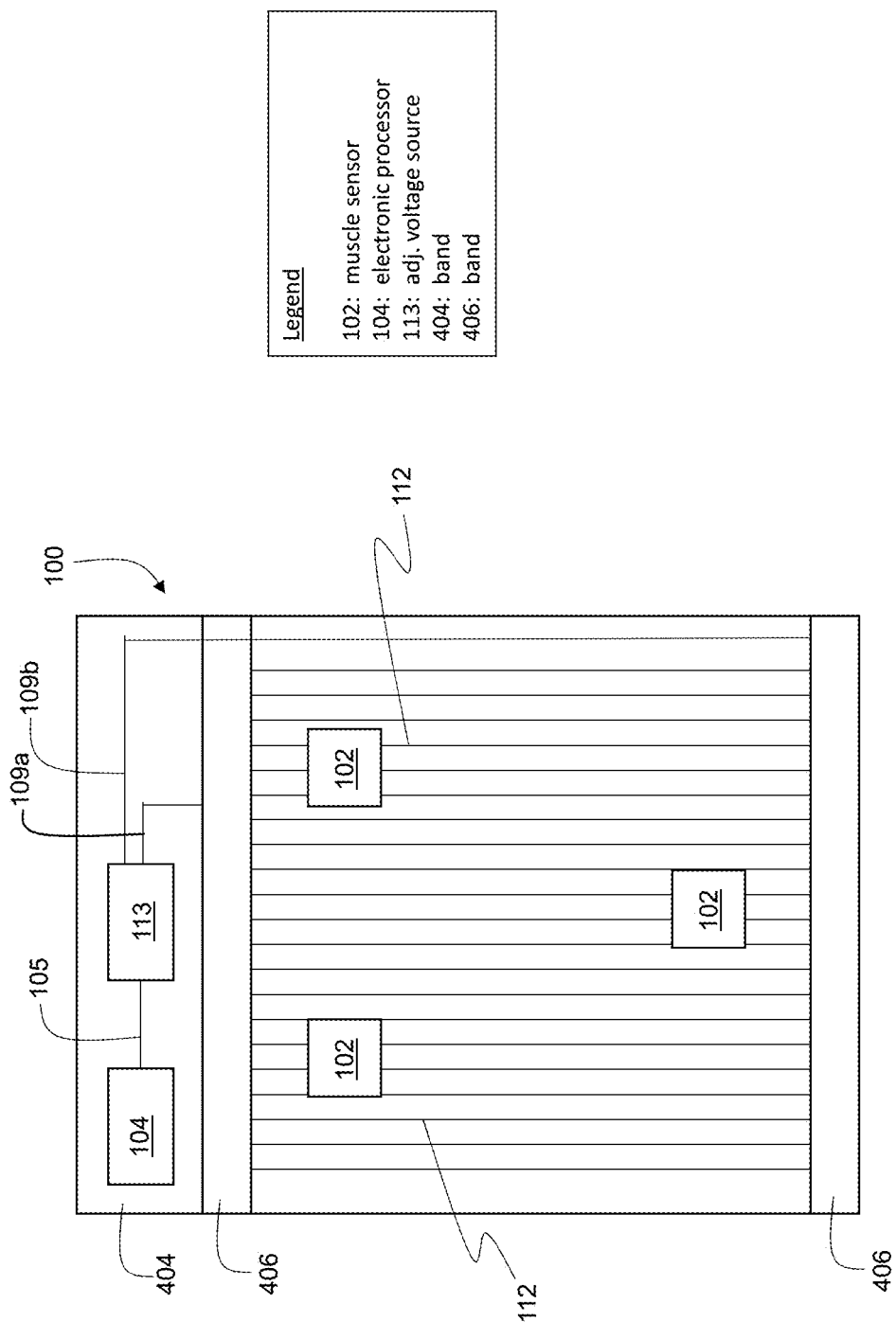
FIG. 12 is a schematic diagram of an example of an adaptive sleeve that includes multiple muscle sensors and groups of deformable elements.

Further, sleeve 100 can include more than one muscle sensor 102. FIG. 12 is a schematic diagram showing a sleeve 100 that includes multiple muscle sensors 102, each connected to electronic processor 104 (connection lines not shown in FIG. 12 for clarity). Within sleeve 100, certain groups of deformable elements 112 correspond to each muscle sensor 102. When electronic processor 104 determines, based on a signal from one of the sensors 102, that a particular muscle or muscle group has contracted, electronic processor 104 selectively activates one or more groups of deformable elements 112 corresponding to the sensor 102 that measured the signal. Thus, electronic processor 104 can be configured to selectively activate multiple groups of deformable elements 112 depending upon the location of the contracted muscles. The number of groups of deformable elements 112 that can be independently controlled by electronic processor 104 can be 2 or more (e.g., 3 or more, 4 or more, 5 or more, 7 or more, 10 or more, or even more).

Figure 13:
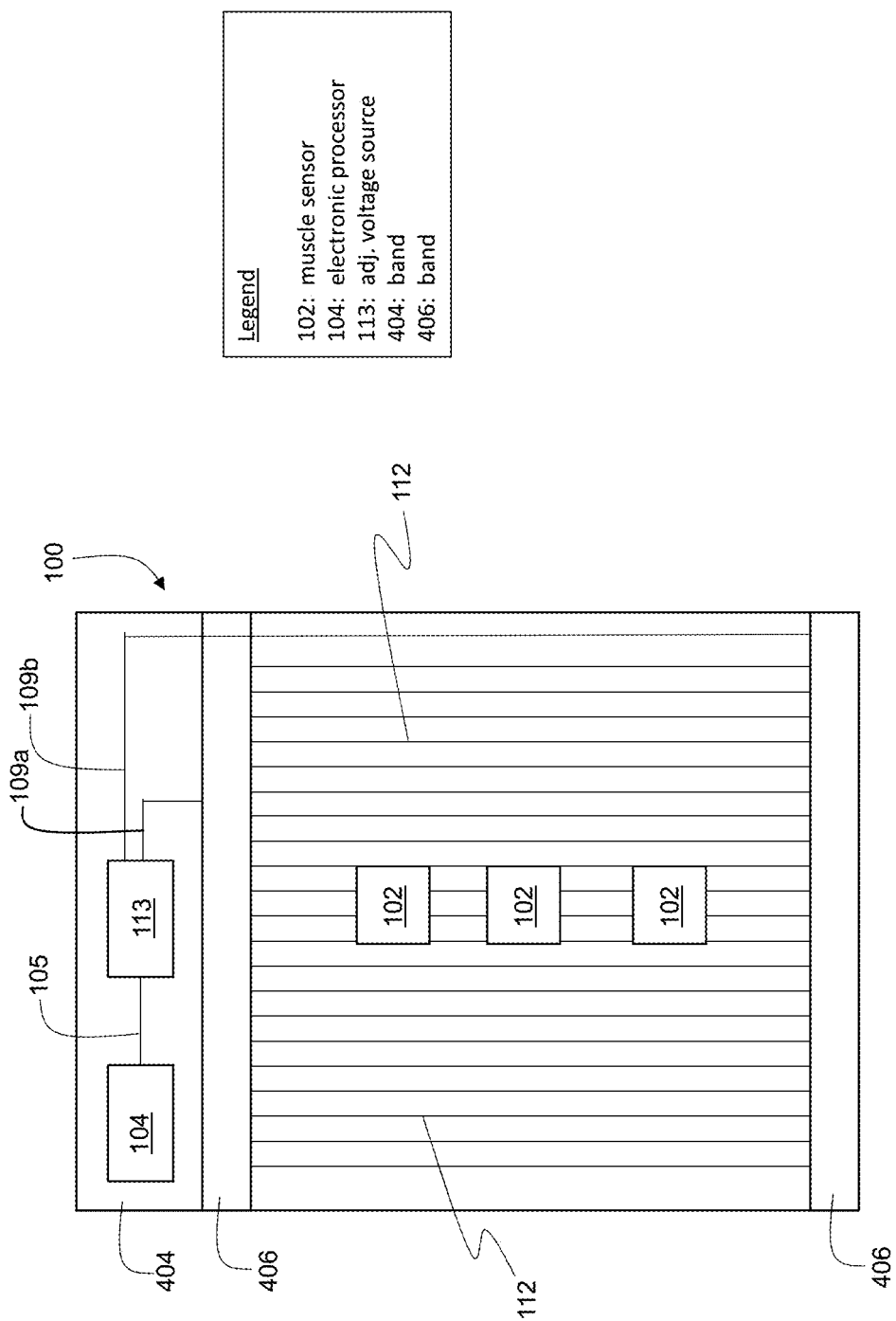
FIG. 13 is a schematic diagram of another example of an adaptive sleeve that includes multiple muscle sensors.
Figure 14:
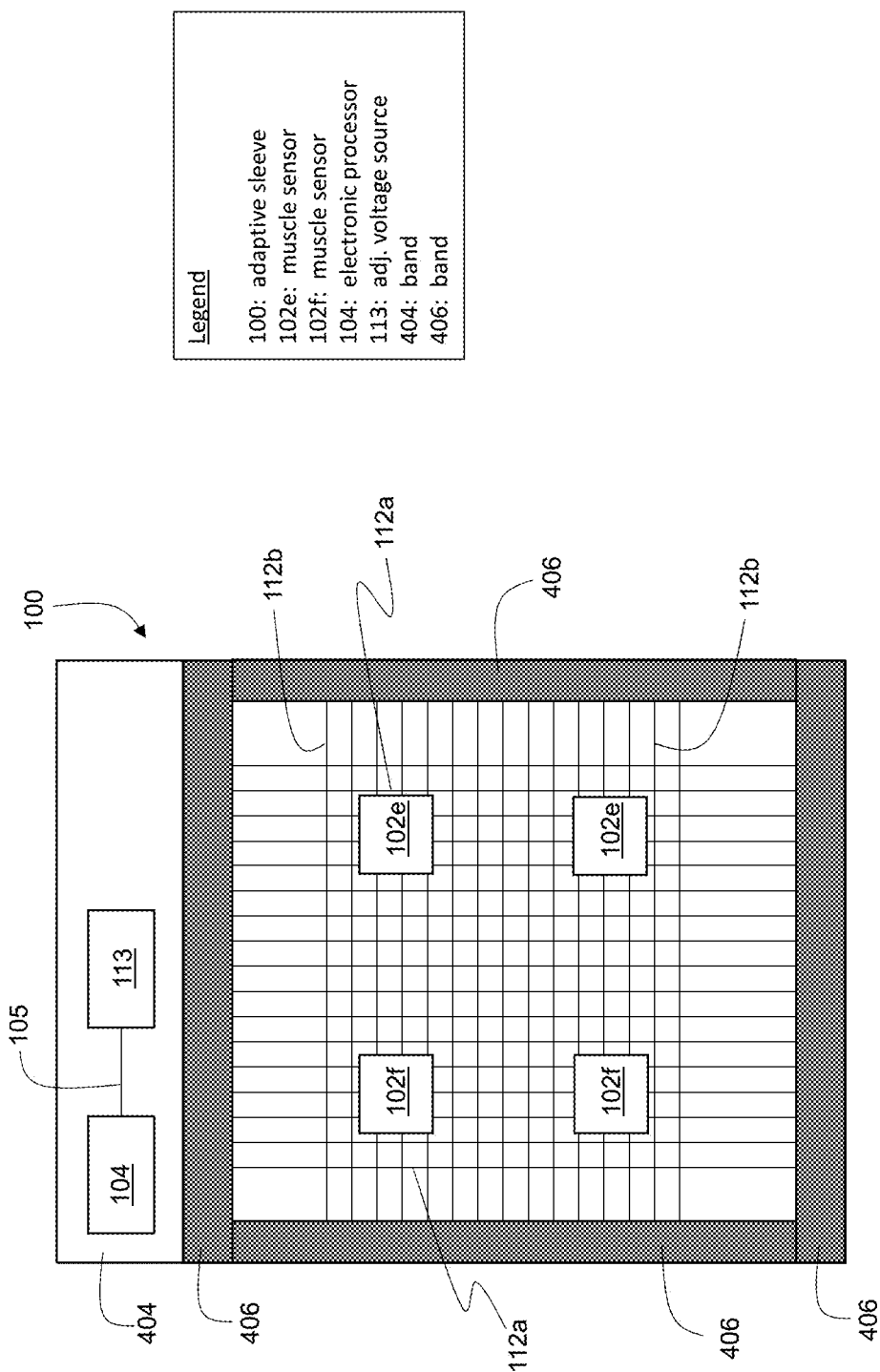
FIG. 14 is a schematic diagram of an example of an adaptive sleeve that includes a network of deformable elements.

In some embodiments, sleeve 100 can include multiple muscle sensors 102 aligned with deformable elements 112, so that electronic processor 104 can vary the extent of contraction of deformable elements 112 along the length of the elements. FIG. 13 is a schematic diagram of a sleeve 100 that includes muscle sensors 102*a-c* aligned along a direction that is approximately parallel to an axial direction of deformable elements 112. Each of sensors 102*a-c* provides a measurement signal to electronic processor 104 corresponding to an extent of muscle contraction in a region of the wearer's body proximal to respective sensors 102*a-c*.

Deformable elements 112 are each constructed such that electronic processor 104 can selectively activate portions of the elements that are proximal to each of sensors 102*a-c*. For example, in some embodiments, deformable elements 112 can include polymer-based coils, where different portions of the polymer-based coils are encircled by independently addressable conductive elements 902, as shown in FIG. 9. Each independent conductive element 902 includes one or more loops surrounding a portion of the polymer coil, and each conductive element 902 can receive an electrical signal from processor 104. Thus, for example, if processor 104 determines that muscle contraction has occurred only in the upper region of sleeve 100 in FIG. 13 (i.e., in proximity to muscle sensor 102*a*), processor 104 can selectively activate only the upper portions of deformable elements 112. If processor 104 determines that muscle contraction has occurred in multiple regions of the wearer's body (e.g., proximal to any two of sensors 102*a-c*, or to all three of the sensors), then processor 104 can selectively activate corresponding portions of deformable elements 112 to apply force to those portions of the wearer's body.

Where multiple portions of deformable elements 112 are activated by processor 104, the processor can also control the extent of activation (e.g., the extent of contraction) of each portion to adaptively regulate the amount of force applied to various portions of the wearer's body. For example, if muscle contraction is strong in proximity to sensor 102*b* but weaker in proximity to sensor 102*c*, electronic processor 104 can adjust the extent of activation of corresponding portions of deformable elements 112 accordingly to provide location-specific support (i.e., force) to the wearer's body.

In some embodiments, sleeve 100 can include a multi-dimensional array of muscle sensors and a corresponding multi-dimensional array of deformable elements 112 to permit more complex applications of force to a wearer's body. Such configurations can be useful, for example, when sleeve 100 is worn over a portion of a user's body that can undertake a variety of complex motion.

FIG. 13 is a schematic diagram of a sleeve 100 that includes a first group of deformable elements 112*a* and a second group of deformable elements 112*b*. The elements of the two groups are aligned along directions that are approximately orthogonal, forming a network of deformable elements. When sleeve 100 is worn over a contoured portion of the body, the network of deformable elements that thus apply a force (e.g., via contraction) along any direction conformal to the body surface. Two muscle sensors 102*e* are associated with deformable elements 112*a*, and two muscle sensors 102*f* are associated with deformable elements 112*b*. When sensors 102*e* detect contraction of a wearer's muscle (e.g., a muscle oriented approximately along the direction of elements 112*a*), electronic processor 104 activates deformable elements 112*a*. When sensors 102*f* detect contraction of a wearer's muscle (e.g., a muscle oriented approximately along the direction of elements 112*b*), electronic processor 104 activates deformable elements 112*b*.

In FIG. 13, two muscle sensors are associated with each group of deformable elements. The two muscle sensors can function in a complementary fashion, to provide verification that a particular muscle or muscle group has contracted, prior to activation of a group of deformable elements. For example, electronic processor 104 may not activate deformable elements 112*a* unless muscle contraction is detected by both sensors 102*e*. In this manner, the use of multiple sensors can provide a mechanism for reducing false positive measurements of muscle contraction. Multiple sensors can be used in any of the embodiments disclosed herein for a similar purpose. Further, in general, any number of muscle sensors 102 (e.g., one or more, two or more, three or more, four or more, five or more, or even more) can be associated with one or more deformable elements in FIG. 13.

Deformable elements 112*a* and 112*b* are oriented approximately orthogonally in FIG. 13. More generally, however, groups of deformable elements 112*a* and 112*b* can be positioned at any orientation relative to one another in sleeve 100 to apply appropriate force in response to muscle contractions. In some embodiments, for example, groups of deformable elements can be oriented within sleeve 100 such that they are approximately aligned with individual muscles or muscle groups within a portion of the wearer's body over which sleeve 100 is intended to be worn.

Although two groups of deformable elements (i.e., 112*a* and 112*b*) are shown in FIG. 13, in general sleeve 100 can include any number of groups of deformable elements (e.g., two or more, three or more, four or more, five or more, or even more), each of which can have its own associated muscle sensor(s), and each of which can be independently activated by electronic processor 104. In some embodiments, for example, sleeve 100 can have a multi-layered structure in which a first group of deformable elements is positioned within a first sleeve layer, a second group of deformable elements is positioned within a second sleeve layer, and so on. In this manner, each group of deformable elements can be electrically isolated within a different sleeve layer, and each group can further be isolated from contact with the deformable elements of other groups.

Furthermore, within each group of deformable elements and between groups of deformable elements, the deformable elements used in sleeve 100 can be the same or different. In general, any combination of the various types of deformable elements discussed herein, and other deformable elements as well, can be used in sleeve 100. In some embodiments, for example, combinations of heat-activated and electrically activated deformable elements can be used. In certain embodiments, to provide for higher resolution control over the applied force, a group of deformable elements (or two different groups of deformable elements) can include a first type of member that contracts over a wide range of distances, and a second type of member that contracts over a smaller range of distances. By selectively activating one type or the other (or both), electronic processor can, in some embodiments, adjust the applied force with higher resolution than would otherwise be possible using a single type of deformable element.

Figure 15:
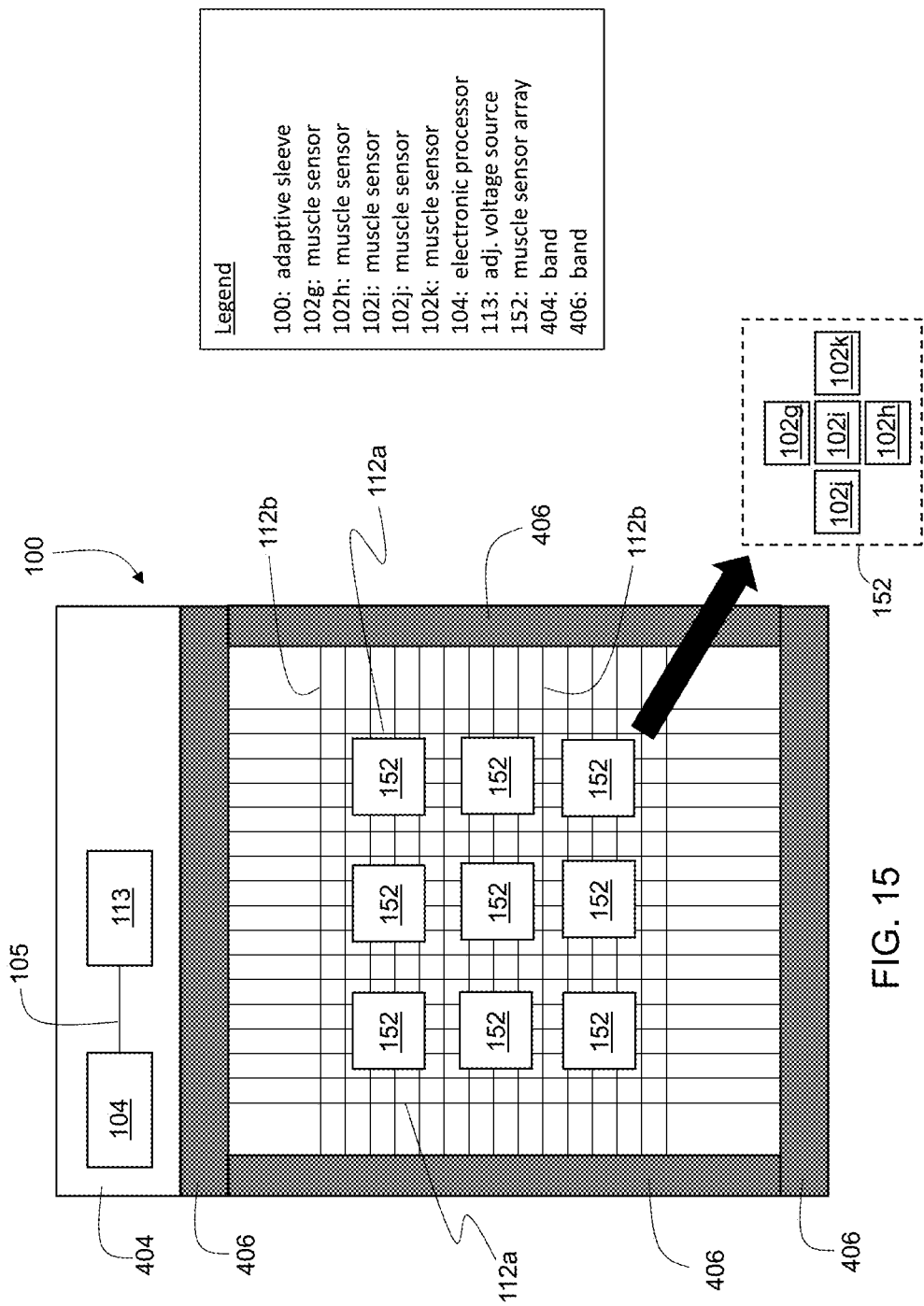
FIG. 15 is a schematic diagram of an example of an adaptive sleeve that includes an array of muscle sensors for vector-based application of force to a wearer's body.

In some embodiments, sleeve 100 can be configured for vector-based operation. FIG. 15 shows a schematic diagram of a sleeve 100 that includes multiple arrays 152 of muscle sensors and an array of individually addressable deformable elements 112. Each of the muscle sensors and deformable elements 112 is electrically connected to electronic processor 104.

During operation, processor 104 receives measurement signals from each of the muscle sensors. Based on the measurement signals from each sensor, processor 104 determines a magnitude and direction of contraction at each location of the wearer's body, and activates deformable elements 112 in a corresponding region of sleeve 100 to apply a force of corresponding magnitude and direction to the wearer's body.

For example, each array 152 can include muscle sensors 102*g-k*, arranged as shown in FIG. 15. Electronic processor 104 receives measurement signals from each of sensors 102*g-k* and determines, based on the magnitudes of the signals, an overall magnitude and direction of muscle contraction corresponding to location of array 152 (e.g., by performing a vector-based combination of the signal magnitudes). Electronic processor 104 then selectively activates deformable elements 112 in the region of array 152 to apply a force along the direction of muscle contraction, the applied force having a magnitude that is correlated with the measured vector magnitude of muscle contraction. Because deformable elements 112 effectively form a network throughout sleeve 100, electronic processor 104—through activation of selected deformable elements 112—can apply a force along any desired direction. In this manner, sleeve 100 can selectively apply forces of adjustable magnitude and direction to different portions of the wearer's body.

Radiation Delivery

In some embodiments, sleeve 100 is also configured to deliver radiation to portions of the wearer's body to promote tissue recovery. FIG. 16 is a schematic cross sectional diagram of a sleeve 100. Certain features of sleeve 100 are not shown in FIG. 16 for clarity. However, it should be appreciated that sleeve 100 can generally include any of the features disclosed previously.

In addition, sleeve 100 includes radiation sources 1602 and radiation detectors 1604. While two sources and two detectors are shown in FIG. 16, it should be appreciated that in general, sleeve 100 can include any number of radiation sources (e.g., one or more sources, two or more sources, three or more source, four or more sources, or even more sources) and detectors (e.g., one or more detectors, two or more detectors, three or more detectors, four or more detectors, or even more detectors) and the number of radiation sources and detectors can be the same or different.

During operation, electronic processor 104 is configured to activate radiation sources 1602 to illuminate a portion of the wearer's body over which sleeve 100 is worn with incident radiation. Typically, the incident light has a central wavelength in the infrared region of the electromagnetic spectrum. Infrared light generally penetrates further into living tissue than visible or ultraviolet light, and can therefore be used for transmission measurements through thicker tissue layers.

Radiation detectors 1604 measure incident radiation that is transmitted through the wearer's body, and the measurements are transmitted to electronic processor 104. Electronic processor 104 determines, based on the measurements of transmitted light provided by radiation detectors 1604, whether inflammation is present in the illuminated tissue of the wearer. This determination can be performed in a variety of ways. When tissue is inflamed, changes in vasculature and blood volume in the region of inflammation commonly occur as part of the body's natural healing process. These changes alter the optical properties of the inflamed tissue relative to normal tissue. Specifically, inflamed tissue can exhibit enhanced optical absorption at certain wavelengths due to larger-than-normal blood volume, as several blood components are relatively strong infrared radiation absorbers. In certain circumstances, inflamed tissue may also exhibit reduced optical absorption at certain infrared wavelengths.

Radiation detectors 1604 are generally configured to measure transmitted infrared radiation at multiple wavelengths. In some embodiments, to determine whether the wearer's tissue is inflamed, electronic processor 104 compares the intensity of measured infrared radiation at one or more wavelengths to a threshold value or expected value. If the measured radiation intensity is less than the threshold value, processor 104 determines that the wearer's tissue is inflamed.

In certain embodiments, electronic processor 104 can make the determination based on a comparison of transmitted radiation intensities at multiple wavelengths. For example, a first radiation detector can be configured to measure radiation intensity at a first wavelength $\lambda_1$ and a second radiation detector can be configured to measure radiation intensity at a second wavelength $\lambda_2$ which is different from $\lambda_1$. Electronic processor 104 may determine that the wearer's tissue is inflamed if the radiation intensity measured at $\lambda_2$ is less than the threshold intensity value at $\lambda_2$, provided that the radiation intensity measured at $\lambda_1$ exceeds the threshold intensity value at $\lambda_1$. In such a scenario, absorption of radiation at $\lambda_1$ is known to be unaffected by tissue inflammation, and so by verifying that the measured radiation intensity is reduced only at $\lambda_2$ and not at $\lambda_1$, false positive detection of inflammation can be reduced.

Similarly, if radiation absorption by inflamed tissue is known to be enhanced at both $\lambda_1$ and $\lambda_2$, electronic processor 104 may determine that the wearer's tissue is inflamed only if the transmitted radiation intensity measured at both $\lambda_1$ and $\lambda_2$ is less than the corresponding threshold values. As above, this comparative procedure can be used to reduce false positive detection of tissue inflammation as a result of other variations in tissue properties, obscuration of the radiation detectors, and other factors that are uncorrelated with inflammation.

If electronic processor 104 determines that the wearer's tissue is inflamed, the electronic processor can activate radiation sources 1602 to deliver therapeutic doses of infrared radiation to the wearer's tissue to promote healing. Without wishing to be bound by theory, it is believed that infrared radiation stimulates cellular mitochondria to enhance ATP production, thereby promoting cellular repair via enhanced oxygenation of affected tissue. It is also believed that infrared radiation promotes internal generation of nitric oxide, enhancing blood flow to the affected tissue.

As explained above, in some embodiments, the number of radiation sources 1602 can differ from the number of radiation detectors 1604. For example, sleeve 100 can include a relatively large number of radiation sources 1602 and a comparatively small number (e.g., one or two) of radiation detectors 1604. One or two of the radiation sources 1602 can be activated to generate infrared radiation to determine whether tissue inflammation is present, as discussed above. If inflammation is detected, electronic processor 104 can activate additional radiation sources 1602 to deliver therapeutic radiation. By operating in this manner, electronic processor 104 conserves power by activating most of the radiation sources 1602 only when therapeutic treatment is appropriate.

In some embodiments, as shown in FIG. 1, sleeve 100 includes a user interface 130 coupled to electronic processor 104 via a control line 132. User interface 130 allows the wearer of sleeve 100 to adjust various operating parameters of the sleeve, including the maximum force applied by sleeve 100, detection threshold values for muscle sensor(s) 102, and a static extent of force applied by sleeve 100, i.e., a "baseline" level of force, which allows the wearer to adjust the static level of "tightness" of sleeve 100. In certain embodiments, user interface 130 can correspond to the user interface of a mobile phone which is wirelessly connected to electronic processor 104 via a network such as a WiFi network or a local Bluetooth network, rather than a control line 132.

Electronic processor 104 is configured to transmit information about inflammation detected via radiation detectors 1604 to user interface 130 (i.e., either to a dedicated interface device or to a mobile phone executing a dedicated application). Processor 104 can transmit inflammation measurement information in real time or near-real time to interface 130, providing a three-dimensional visualization of inflammation measurements for a portion of the wearer's body. Further, user interface 130 can include controls that allow the wearer to adjust the threshold radiation intensity levels associated with radiation detectors 1604, to adjust the intensity of radiation generated by sources 1602 for measurement of tissue inflammation, and to adjust the intensity of radiation generated by sources 1602 for therapeutic healing of tissue.

Modes of Operation

The sleeves disclosed herein can operate in different modes, depending upon the nature of the support that is desired for the wearer. For example, the sleeves can operate in a first "assistive" mode in which the applied force assists muscle contraction. In this mode of operation, when the wearer's muscles contract, sleeve 100 applies a complementary force to the wearer's body that assists contraction-based motion of the wearer's body, thereby augmenting the action of the wearer's musculature. This mode of operation can be useful when sleeve 100 is worn during injury rehabilitation and/or as an assistive device for elderly, infirm, and/or otherwise compromised individuals.

The sleeves can also operate in a second "resistive" mode in which the applied force counteracts motion of the wearer's body. In this mode of operation, when the wearer's muscles contract suggesting movement of the body is imminent, sleeve 100 applies a force to counteract the anticipated movement of the wearer's body, thereby stabilizing the portion of the body over which sleeve 100 is worn. This mode of operation can be useful, for example, when sleeve 100 is worn as a supportive device over injured muscles or tissue to prevent further damage to the muscles/tissue. Sleeve 100 effectively functions as an immobilizing device, which allows the injured muscles/tissue to heal.

As discussed above, sleeve 100 includes a user interface 130 coupled to electronic processor 104, which can be a dedicated interface attached to sleeve 100 or an interface such as a mobile phone executing a dedicated application and connected to electronic processor via a network connection such as a WiFi or Bluetooth connection. User interface 130 can include a control that allows the wearer of sleeve 100 to select the mode of operation of sleeve 100 (i.e., assistive or resistive). In some embodiments, electronic processor 104 can also suggest a mode of operation of sleeve 100 based on, for example, a time history of activation of the deformable elements of sleeve 100, and user interface 130 can include a control that allows the wearer to accept or reject the suggested mode of operation.

Applications

As discussed above, sleeve 100 can be configured for wear on a variety of different portions of the body, including on a user's knee, ankle, thigh, hip, back, shoulder, elbow, wrist, chest, and forearm. At each location, sleeve 100 can be configured to selectively and adaptively apply force to the wearer's body in response to muscle contractions, either to aid movement of the wearer's body as a product of the muscle contractions, or to oppose movement of the wearer's body, thereby stabilizing his or her body against certain movements. Sleeve 100 can thus be used as a compression brace to support or promote healing of damaged tissues, muscles, and joints, and/or an assistive device to augment the wearer's existing musculature. As an assistive device, sleeve 100 can provide enhanced motor control and stability to the wearer, which can be particularly useful for elderly or infirm patients.

Although sleeve 100 is shown in this disclosure as a tubular member configured to wrap around or surround a portion of the wearer's body, it should be appreciated that sleeve 100 is not limited to such shapes. As sleeve 100 is typically worn on a portion of the human body, sleeve 100 can generally have any shape that conforms to one or more portions of the body. For example, sleeve 100 can have a shape that corresponds to an article of clothing, such as a pair of shorts, a pair of pants, tights, and a shirt. Sleeve 100 can also generally have any other shape that can be secured to a portion of the wearer's body. Where sleeve 100 is large enough to cover multiple portions of a wearer's body to which force will be applied, sleeve 100 can optionally include muscle sensors 102, deformable elements 112, and any of the other components discussed herein at each location on sleeve 100 that corresponds to a portion of the wearer's body to which force will be applied.

In some embodiments, sleeve 100 can be implemented as an entire bodysuit that extends from a wearer's lower extremities (i.e., ankles, calves, knees) to the wearer's upper extremities (i.e., shoulders, neck). When implemented as a bodysuit, sleeve 100 can include groups of muscle sensors 102 and deformable elements 112 that are positioned to correspond to the locations of major muscle groups within the wearer's body. Deformable elements 112 can be used to enhance the wearer's musculature, augmenting the wearer's natural muscle strength.

A bodysuit of this nature can be particularly useful in applications where fatigue is an important consideration. For example, for pilots and astronauts performing activities in reduced oxygen environments, muscle fatigue and concomitant muscular weakness can arise after prolonged periods of physical activity. A sleeve 100 configured as a bodysuit and worn underneath a flight suit or spacesuit can enhance the pilot's or astronaut's natural musculature, compensating for fatigue and ensuring that the pilot or astronaut remains capable of physically performing a variety of muscle-intensive tasks.

Hardware and Software Implementation

The processing and control functions described herein can be implemented in an electronic processor (e.g., electronic processor 104), in an electronic control system, in digital electronic circuitry, or in computer hardware, firmware, or in combinations of these. The features can be implemented in a computer program product tangibly embodied in an information carrier, e.g., in a machine-readable storage device, for execution by a programmable processor (e.g., processor 104); and features can be performed by a programmable processor (e.g., processor 104) executing a program of instructions to perform functions of the described implementations by operating on input data (e.g., input electrical signals) and generating output data (e.g., output electrical signals). The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable electronic processors for the execution of a program of instructions include, by way of example, both general and special purpose microprocessors, and the sole processor or one of multiple processors of any kind of computer or computing device. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

In some embodiments, the sleeves disclosed herein can include any one or more of the foregoing storage devices, and user interface components such as touchscreen displays and other input and output devices to facilitate communicating information to a user and receiving information and/or commands from the user.

Components of the sleeves can be connected by any form or medium of digital data communication such as a communication network. Examples of communication networks include, e.g., a LAN, a WAN, a cellular network, the computers and networks forming the Internet, and local short-distance communication networks such as Bluetooth networks. In particular, electronic processor 104 can be connected wirelessly via any of the foregoing networks to a user interface, e.g., a display on mobile phone that is executing a specific application that interfaces with electronic processor 104 to receive data from, and transmit data to, electronic processor 104. The sleeves can include a wireless communication interface integrated into the sleeve and connected to electronic processor 104.

Other Embodiments

While examples have been provided for purposes of explanation, combinations, substitutions and alterations can be made without deviating from the spirit of the disclosure, and it is intended that the scope of the disclosure be limited only by the claims appended hereto.

What is claimed is:

1. An adaptive sleeve, comprising:
   a sensor configured to generate an electrical signal in response to contraction of a muscle;
   an electronic processor connected to the sensor;
   an adjustable voltage source connected to the electronic processor; and
   a sleeve formed of a fabric material and comprising one or more deformable elements attached to or embedded within the fabric material and connected to the adjustable voltage source,
   wherein during operation of the adaptive sleeve, the electronic processor is configured to apply a compressive force to a portion of a body of a sleeve wearer in proximity to a contracted muscle in the wearer's body by:
      receiving an input electrical signal from the sensor indicative of contraction of the muscle; and
      adjusting the voltage source to apply an output electrical signal to the one or more deformable elements to activate the one or more deformable elements, the output electrical signal having a magnitude that is correlated with a magnitude of the input electrical signal, and the applied output electrical signal causing the one or more deformable elements to contract, thereby applying a compressive force to the portion of the body of the sleeve wearer that is larger than a compressive force applied by the one or more deformable elements in an un-activated state; and
   wherein at least one of the one or more deformable elements comprises:
      a twisted filament formed of at least one polymer material arranged in a helical coil, the twisted filament being configured to undergo a reduction in length along an axial direction of the helical coil in response to heating of the filament by the application of the output electrical signal; and
      an electrically conductive wire wrapped around the twisted filament; and
   wherein the electrically conductive wire comprises multiple pluralities of helical loops separated by non-looped portions of the conductive wire that connect adjacent pluralities of loops, and each adjacent pair of pluralities of loops is separated by a distance of a non-looped portion of the conductive wire that is at least twice a diameter of the electrically conductive wire, wherein each non-looped portion extends parallel to a longitudinal direction of the twisted filament.

2. The sleeve of claim 1, wherein the adjustable voltage source comprises a power supply, an adjustable servo motor, and a potentiometer.

3. The sleeve of claim 1, wherein at least some of the one or more deformable elements are aligned along a common direction within the fabric material.

4. The sleeve of claim 1, wherein at least one portion of the fabric material comprises no deformable elements and is configured to be positioned over a joint in the body of the sleeve wearer.

5. The sleeve of claim 1, wherein each adjacent pair of pluralities of loops is separated by a distance of the non-looped portion of the conductive wire that is at least 5 times the diameter of the electrically conductive wire.

6. The sleeve of claim 1, wherein at least some of the deformable elements comprise a plurality of coils of conductive material mechanically and electrically connected together.

7. The sleeve of claim 1, wherein the deformable elements are positioned within the fabric material so that when contraction of the muscle occurs along a first direction, the one or more deformable elements contract at least partially along the first direction.

8. The sleeve of claim 1, wherein the magnitude of the output electrical signal is linearly proportional to the magnitude of the input electrical signal.

9. The sleeve of claim 1, wherein the magnitude of the output electrical signal is non-linearly correlated with the magnitude of the input electrical signal.

10. The sleeve of claim 1, further comprising one or more electrodes connecting the one or more deformable elements to the adjustable voltage source, wherein the one or more electrodes comprise electrical conductors embedded within the fabric material.

11. The sleeve of claim 1, wherein the sensor is a first sensor and the one or more deformable elements are a first set of deformable elements, the sleeve further comprising:
    a second sensor connected to the electronic processor and configured to generate an electrical signal in response to contraction of a muscle; and
    a second set of one or more deformable elements attached to or embedded within the fabric material and connected to the adjustable voltage source,
    wherein during operation of the adaptive sleeve, the electronic processor is configured to:
       receive input electrical signals from the first and second sensors;
       determine which of the first and second sets of deformable elements to activate based on the input electrical signals; and
       adjust the voltage source to apply output electrical signals to one or both of the first and second sets of deformable elements, thereby applying the compressive force to the portion of the body of the sleeve wearer.

12. The sleeve of claim 11, wherein at least some of the first set of deformable elements correspond to a first type of deformable element, and at least some of the second set of deformable elements correspond to a second type of deformable element different from the first type.

13. The sleeve of claim 11, wherein the electronic processor is configured to adjust the voltage source to apply different output electrical signals to the first and second sets of deformable elements, and wherein magnitudes of the different output electrical signals are correlated with magnitudes of the input electrical signals from the first and second sensors, respectively.

14. The sleeve of claim 11, wherein at least some members of the first set of deformable elements are aligned along a first direction in the sleeve, and at least some members of the second set of deformable elements are aligned along a second direction in the sleeve that is different from the first direction.

\* \* \* \* \*